US007214686B2

(12) United States Patent
Bencherif et al.

(10) Patent No.: US 7,214,686 B2
(45) Date of Patent: May 8, 2007

(54) PHARMACEUTICAL COMPOSITIONS AND METHODS FOR EFFECTING DOPAMINE RELEASE

(75) Inventors: Merouane Bencherif, Winston-Salem, NC (US); Craig Harrison Miller, Winston-Salem, NC (US); Gregory D. Hawkins, Winston-Salem, NC (US); Balwinder S. Bhatti, Winston-Salem, NC (US)

(73) Assignee: Targacept, Inc., Winston-Salem, NC (US)

( * ) Notice: Subject to any disclaimer, the term of this patent is extended or adjusted under 35 U.S.C. 154(b) by 429 days.

(21) Appl. No.: 10/454,292

(22) Filed: Jun. 4, 2003

(65) Prior Publication Data
US 2004/0220214 A1    Nov. 4, 2004

Related U.S. Application Data

(63) Continuation-in-part of application No. 08/885,768, filed on Jun. 30, 1997, now Pat. No. 6,624,173.

(51) Int. Cl.
C07D 451/00 (2006.01)
A61K 31/55 (2006.01)

(52) U.S. Cl. .................. 514/305; 546/137; 546/133; 546/268.1

(58) Field of Classification Search .............. 546/97, 546/268.1, 133, 137; 514/305
See application file for complete search history.

(56) References Cited

U.S. PATENT DOCUMENTS

| | | | | |
|---|---|---|---|---|
| 4,921,982 A * | 5/1990 | Cohen et al. | ............... | 549/462 |
| 4,922,901 A | 5/1990 | Brooks et al. | .......... | 128/203.26 |
| 4,952,229 A | 8/1990 | Muir | | |
| 4,965,074 A | 10/1990 | Leeson | ................. | 424/449 |
| 5,164,386 A * | 11/1992 | Cereda et al. | .......... | 514/212.08 |
| 5,187,166 A | 2/1993 | Kikuchi et al. | ............. | 514/249 |
| 5,210,076 A | 5/1993 | Berliner et al. | .............. | 514/21 |
| 5,212,188 A | 5/1993 | Caldwell et al. | ............ | 514/343 |
| 5,227,391 A | 7/1993 | Caldwell et al. | ............ | 514/343 |
| 5,242,935 A | 9/1993 | Lippiello et al. | ........... | 514/343 |
| 5,346,906 A * | 9/1994 | Baker et al. | ............... | 514/305 |
| 5,488,056 A * | 1/1996 | Bodick et al. | .............. | 514/305 |
| 5,510,355 A | 4/1996 | Bencherif et al. | ........... | 514/305 |
| 5,552,138 A | 9/1996 | Handelsman et al. | | |
| 5,559,124 A | 9/1996 | Bencherif et al. | ........... | 514/305 |
| 5,583,140 A | 12/1996 | Bencherif et al. | ........... | 514/299 |
| 5,597,919 A | 1/1997 | Dull et al. | .................. | 544/242 |
| 5,604,231 A | 2/1997 | Smith et al. | ................. | 514/256 |
| 5,616,716 A | 4/1997 | Dull et al. | .................. | 546/300 |
| 5,663,356 A | 9/1997 | Ruecroft et al. | ............. | 546/300 |
| 5,672,601 A | 9/1997 | Cignarella | .................. | 514/249 |
| 5,702,703 A | 12/1997 | Schnepf et al. | | |
| 5,753,222 A | 5/1998 | Marrone et al. | | |
| 5,852,038 A * | 12/1998 | Ito et al. | ...................... | 514/305 |
| 5,852,041 A | 12/1998 | Cosford et al. | ............. | 514/351 |
| 5,853,696 A | 12/1998 | Elmaleh et al. | ............ | 424/1.85 |
| 5,969,144 A | 10/1999 | London et al. | ........... | 546/276.7 |
| 6,057,446 A * | 5/2000 | Crooks et al. | ................ | 546/97 |
| 6,194,193 B1 | 2/2001 | Drahos et al. | | |
| 6,228,806 B1 | 5/2001 | Mehta | | |
| 6,310,043 B1 | 10/2001 | Bundle et al. | ................ | 514/25 |
| 6,311,426 B1 | 11/2001 | Mehta et al. | | |
| 2001/0056084 A1 | 12/2001 | Allgeier et al. | ............. | 514/151 |
| 2003/0092700 A1 | 5/2003 | Czollner et al. | ....... | 514/217.01 |

FOREIGN PATENT DOCUMENTS

| | | |
|---|---|---|
| EP | 0 297 858 A2 | 4/1989 |
| EP | 0 588 917 B1 | 11/2000 |
| GB | 2 295 387 A | 5/1996 |
| JP | 363051398 A | 3/1988 |
| WO | WO 94/08992 | 4/1994 |
| WO | WO 96/30372 | 10/1996 |
| WO | WO 96/31475 | 10/1996 |
| WO | WO 97/30998 | 8/1997 |
| WO | WO 98/25619 | 6/1998 |
| WO | WO 99/03859 | 1/1999 |
| WO | WO 99/21834 | 5/1999 |
| WO | WO 99/62505 | 12/1999 |
| WO | WO 00/73431 | 12/2000 |

(Continued)

OTHER PUBLICATIONS

Sivaman et al.; Influence of some plant phenolics on the activity of delta endotoxin of *Bacillus thuringiensis* var. *galleria* on *Helithis armigera*; Entomologia Experimentalis et applicata. 1992, vol. 63, pp. 243-248.

(Continued)

*Primary Examiner*—Sabiha N. Qazi
(74) *Attorney, Agent, or Firm*—Womble Carlyle Sandridge & Rice, PLLC

(57) ABSTRACT

Patients susceptible to or suffering from disorders, such as central nervous system disorders, which are characterized by an alteration in normal neurotransmitter release, such as dopamine release (e.g., Parkinsonism, Parkinson's Disease, Tourette's Syndrome, attention deficient disorder, or schizophrenia), are treated by administering a 1-aza-2-(3-pyridyl) bicyclo[2.2.1]heptane, a 1-aza-2-(3-pyridyl)bicyclo[2.2.2] octane, a 1-aza-2-(3-pyridyl)bicyclo[3.2.1]octane, a 1-aza-2-(3-pyridyl)bicyclo[3.2.2]nonane, a 1-aza-7-(3-pyridyl) bicyclo[2.2.1]heptane, a 1-aza-3-(3-pyridyl)bicyclo[3.2.2] nonane, or a 1-aza-7-(3-pyridyl)bicyclo[3.2.2]nonane. The compounds can exist as individual stereoisomers, racemic mixtures, diastereomers and the like.

2 Claims, No Drawings

FOREIGN PATENT DOCUMENTS

| WO | WO 01/36417 | 5/2001 |
|---|---|---|
| WO | WO 01/82978 | 11/2001 |
| WO | WO 02/15662 | 2/2002 |
| WO | WO 02/16355 | 2/2002 |
| WO | WO 02/16356 | 2/2002 |
| WO | WO 02/16357 | 2/2002 |
| WO | WO 02/16358 | 2/2002 |
| WO | WO 02/17358 | 2/2002 |

OTHER PUBLICATIONS

Kelada et al.; Toxicity of Three Chemical Insecticides in combination with *Bacillus* spp. Against Mosquito Larvae; Insect Science Application ; 1988, vol. 9, pp. 229-230.

Asano et al.; Progidiosin Produced by *Serratia marcescens* enhances the insecticidal activity of *Bacillus thuringlensis* delta endotoxin (CrylC) against common cutworm, Spodoptera litura; Journal of Pesticide Science; 1999, vol. 24, pp. 381-385.

Pramanik et al.; Persistence Toxicity of *Bacillus thurigiensts* Ver Kurstaki in Combination with some Chemical Additives Under Field Condition; Environment and Ecology, vol. 18, No. 1, Mar. 2000, pp. 114-118.

Adler, L.E., et al., "Normalization by Nicotine of Deficient Auditory Sensory Gating to the Relatives of Schizophrenics," *Biol. Psychiatry*, 32(7):607-616 (1992).

Arneric, S.P., et al., "Preclinical Pharmacology of ABT-418: A Prototypical Cholinergic Channel Activator to the Potential Treatment of Alzheimer's Disease," *CNS Drug Rev.*, 1(1): 1-26 (1995).

Arneric, S.P., et al., "Cholinergic channel modulators as a novel therapeutic strategy for Alzheimer's disease," *Exp. Opin. Invest. Drugs*, 5(1): 79-100 (1996).

Ashimori, A., et al., "Novel 1,4-Dihydropyridine Calcium Antagonists. I. Synthesis and Hypotensive Activity of 4-(Substituted Pyridyl)-1,4-dihydropyridine Derivatives," *Chem. Pharm. Bull.*, 38(9): 2446-2458 (1990).

Bannon, A.W., et al., "Broad-Spectrum, Non-Opioid Analgesic Activity by Selective Modulation of Neuronal Nicotinic Acetylcholine Receptors," *Science*, 279: 77-80 (1998).

Baron, J.A., "Cigarette smoking and Parkinson's disease," *Neurology*, 36: 1490-1496 (1986).

Bencherif, M., and J. D. Schmitt, "Targeting Neuronal Nicotinic Receptors: a Path to New Therapies," *Current Drug Targets*, 1(4): 349-357 (2002).

Bencherif, M., amd R.J. Lukas, "Ligand Binding and Functional Characterization of Muscarinic Acetylcholine Receptors on the TE671/RD Human Cell Line," *J. Pharmacol. Exp. Ther.*, 257(3): 946-953 (1991).

Bancherif, M., et al., "RJR-2403: A Nicotinic Agonist with CNS Selectively I: In Vitro Characterization," *J. Pharmacol. Exper. Therapeutics, 279(3)*: 1413-1421 (1996).

Bencherif M. and R.J. Lukas, "Differential Regulation of Nicotinic Acetylcholine Receptor Expression by Human TE67/RD Cells Following Second Messenger Modulation and Sodium Butyrate Treatments," *Mol. Cell. Neurosci.*, 2(1): 52-65 (1991).

Brioni, J.D., et al., "The Pharmacology of (—)-Nicotine and Novel Cholinergic Channel Modulators," *Adv. Pharmacol.*, 37: 153-214 (1997).

Burger, A., et al., "Some Derivatives of Tetrohydropyran as Potential Pharmacodynamic Agents," *J. Amer. Chem. Soc.*, 72: 5512-5515 (1950).

Calderon-Gonzalez, R., and R.F. Calderon-Sepulveda, "Tourette Syndrome Current Concepts," *Intern. Pediat.*, 8(2): 176-188 (1993).

Chen, Y., et al., "Asymmetric Synthesis VIII: Enantioselective Synthesis of (R) or (S) —Substituted Benzylamines Via Chiral Pinanone Ketimine Template," *Synth. Comm.*, 19(7&8): 1423-1430 (1989).

Cheng, Y., and W.H. Prusoff, "Relationship Between the Inhibition Constant ($K_1$) and the Concentration of Inhibitor which Causes 50 Per Cent inhibition ($I_{50}$) of an Enzymatic Reaction," *Biochem. Pharmacol.*, 22(23): 3099-3108 (1973).

Chiari, A., et al., "Sex Differences in Cholinergic Analgesia I: A Supplemental Nicotinic Mechanism in Normal Females," *Anesthesiology*, 91(5): 1447-1454 (1999).

Clarke, P.B.S., et al., "Electrophysiological actions of nicotine on substantia nigra single units," *Br. J. Pharm.*, 85(4): 827-835 (1985).

Comins, D. L., and M.O. Killpack, "Lithiation of Methoxypyridines Directed by α-Amino Alkoxides," *J. Org. Chem.*, 55(1): 69-73 (1990).

Cosford, N.D.P., et al., "(S)-(—) 5- Ethynyl-3-(1-methyl-2-pyrrolidinyl) pyridine Maleate (SIB-1508Y): A Novel Anti-Parkinsonian Agent with Selectivity for Neuronal Nicotinic Acetylcholine Receptors," *J. Med. Chem.*, 39(17) : 3235-3237 (1996).

Damaj, M.I., et al., "Antinociceptive and Pharmacological Effects of Metanicotine, a Selective Nicotinic Agonist," *J. Pharmacol. Exp. Ther.*, 291(1): 390-398 (1999).

Davies, A.R.L., et al., "Characterisation of the binding of [$^3$H]methyllycaconitine: a new radioligand for labeling α7-type neuronal nicotinic acetylcholine receptors," *Neuropharmacol.*, 38: 679-690 (1999).

Decina, P., et al., "Cigarette Smoking and Neuroleptic-Induced Parkinsonism," *Biol. Psychiatry, 28(6)*: 502-508 (1990).

De Kimpe, N.G., et al., "Synthesis of Cyclic Imines via Ethyleneteramethyldisilyl-Protected ω-Aminoimines, Application to the Synthesis of Alkaloids," *Tet. Lett.*, 34(29): 4693-4696 (1993).

Devor, E.J., and K.E. Isenberg, "Nicotine and Tourette's Syndrome," *The Lancet*, 2(8670): 1046(1989).

Dolle, F., et al., "Synthesis and preliminary evaluation of a cardon-11-labelled agonist of the α-7 nicotinic acetylcholine receptor," *J. Labelled Comp. Radiopharm.*, 44:785-795 (2001).

Dwoskin, L.P., et al., "Recent developments in neuronal nicotinic acetylcholine receptor antagonists," *Exp. Opin. Ther. Patents*, 10(10): 1561-1581 (2000).

Enders, D., and U. Reinhold, "Diastereo- and Enantioselective Synthesis of 1,2-Amino Alcohols and Protected α-Hydroxy Aldehydes from Glycol Aldehyde Hydrazones," *Liebigs Ann.*, (1): 11-26 (1996).

Enders, D., and D.L. Whitehouse, "Highly Enantioselective α-Alkenylation of Aldehydes and Ketones," *Synthesis*, (5): 621-626 (1996).

Faraone, S.V., et al., "An Exploratory Study of ADHD among Second-Degree Relatives of ADHD Children," *Biol. Psychiatry*, 35(6): 398-402 (1994).

Freedman, R., et al., "Evidence in Postmortem Brain Tissue for Decreased Numbers of Hippocampal Nicotinic Receptors in Schizophrenia," *Biol. Psychiatry*, 38(1): 22-33 (1995).

Freedman, R., et al., "Linkage of a neurophysiological deficit in schizophrenia to a chromosome 15 locus," *Proc. Natl. Acad. Sci.*, 94: 587-592 (1997).

Giacobini, E., "Cholinergic Receptors in Human Brain: Effects of Aging and Alzheimer Disease," *J. Neurosci. Res.*, 27(4): 548-560 (1990).

Gibson, S. et al., "Principal Components Describing Biological Activities and Molecular Diversity of Heterocyclic Aromatic Ring Fragments," *J. Med. Chem.*, 39(20): 4065-4072 (1996).

Glassman, A.H., "Cigarette Smoking: Implications for Psychiatric Illness," *Amer. J. Psychiatry*, 150(4): 546-553 (1993).

Hall, G.H. and D.M. Turner, "Effects of Nicotine on the Release of $^3$H-Noradrenaline from the Hypothalamus," *Biochemical Pharmacology*, 21: 1829-1838 (1972).

Hamon, M., "Neuropharmacology of anxiety: perspectives and prospects," *TiPS*, 15: 36-39 (1994).

Hansch, C., et al., "A Survey of Hammett Substituent Constants and Resonance and Field Parameters," *Chem. Rev.*, 91(2): 165-195 (1991).

Harsing, Jr., L.G., et al., "Dopamine Efflux from Striatum After Chronic Nicotine: Evidence for Autoreceptor Desensitization," *J. Neurochem.*, 59(1): 48-54 (1992).

Hechtman, L., "Genetic and Neurobiological Aspects of Attention Deficit Hyperactive Disorder. A Review" *J. Psychiatry Neurosci*, 19(3): 193-201 (1994).

Heeschen, C., et al., "A novel angiogenic pathway mediated by non-neuronal nicotinic acetylcholine receptors," *J. Clin. Invest.*, 110(4): 527-536 (2002).

Hertog, H.J.D., et al., "The Directive Influences of the N-Oxide Group During the Nitration of Derivatives of Pyridine N-Oxide (IV) [1]) Nitration of 3-bromo-5methoxy- and 3,5-dimethoxy-pyridine-N-oxide[2])," Recueil Trav. Chem. Pays-Bas, 74(8/9): 1171-1179 (1955).

Hery, F., et al., "Control of the Release of Newly Synthetized [3]H-5-Hydroxytryptamine by Nicotinic and Muscarinic Receptors in Rat Hypothalamic Slices," Naunyn-Schmiedeberg's Arch. Pharmacol., 296: 91-97 (1977).

Hoffman, J.M., et al., "Synthesis and Evaluation of 2-Pyridinone Derivatives as HIV-1-Specific Reverse Transcriptase Inhibitors. 4. 3-[2-(Benzoxazol-2-yl)ethyl]-5-ethyl-6-methylpyridin-2(1H)-one and Analogues," J. Med. Chem., 36: 953-966 (1993).

Holladay, M.W., et al., "Neuronal Nicotinic Acetylcholine Receptors as Targets for Drug Discovery," J. Med. Chem., 40(26): 4169-4194 (1997).

Hoyer, D. and H.W.G.M. Boddeke, "Partial agonists, full agonists, antagonists: dilemmas of definition," TiPS Reviews, 14: 270-275 (1993).

Hughes, D.L., "The Mitsunobu Reaction," Org. React., 42: 335-657 (1992).

Hughes, D.L., "Progress in the Mitsunobu Reaction. A Review," Org. Prep. Proced. Int., 28(1): 129-164 (1996).

Jarvik, M.E., "Beneficial effects of nicotine," Brit. J. of Addic., 571-575 (1991).

Jeyarasasingam, G., et al., "Stimulation of Non-α7 Nicotinic Receptors Partially Protects Dopaminergic Neurons from 1-Methyl-4 Phenlypyridinium-Induced Toxicity in Culture," Neuroscience, 109(2): 275-285 (2002).

Jones, A.W.R., and J.S. Richardson, "Alzheimer's Disease: Clinical and Pathological Characteristics," Intern. J. Neurosci., 50(3-4): 147-168 (1990).

Lavand'homme, P.M., and J.C. Eisenach, "Sex Differences in Cholinergice Analgesia II: Differing Mechanisms in Two Models of Allodynia," Anesthesiology, 91(5): 1455-1461 (1999).

Leonard, S., et al., "Nicotinic Receptor Function in Schizophrenia," Schizophrenia Bulletin, 22(3), 431-445 (1996).

Levin, E.D., et al., "Nicotine effects on adults with attention-deficit/hyperactivity disorder," Psychopharmacology, 123: 55-63 (1996).

Levin, E.D., and A.H. Rezvani, "Nicotinic Treatment for Cognitive Dysfunction," Current Drug Targets: CNS and Neurological Disorders, 1(4): 423-431 (2002).

Lieberman, J.A., and A.R. Koreen, "Neurochemistry and Neuroendocrinology of Schizophernia: A Selective Review," Schizophr. Bull., 19(2): 371-429 (1993).

Lippiello, P.M., et al., "RJR-2403: A Nicotinic Agonist with CNS Selectivity II. In Vivo Characterization," J. P. E. T., 279(3): 1422-1429 (1996).

Lowry, O.H., et al., "Protein Measurement with the Folin Phenol Reagent," J. Biol. Chem., 193: 265-275 (1951).

Lukas, R.J., and M.J. Cullen, "An Isotopic Rubidium Ion Efflux Assay for the Functional Characterization of Nicotinic Acetylcholine Receptors on Clonal Cell Lines," Anal. Biochem., 175(1): 212-218 (1988).

Lukas, R.J., "Pharmacological Distinctions between Functional Nicotinic Acetylcholine Receptors on the PC12 Rat Pheochromocytoma and the TE671 Human Medulloblastoma," J. Pharmacol. Exp. Ther., 251(1): 175-182 (1989).

Lukas, R.J., et al., "Characterization of Nicotinic Acetylcholine Receptors Expressed by Cells of the SH-SY5Y Human Neuroblastoma Clonal Line," Molec. Cellular Neurosci., 4(1): 1-12 (1993).

Luther, M.A., et al., "A Muscle Acetylcholine Receptor is Expressed in the Human Cerebellar Medulloblastoma Cell Line TE671," J. Neurosci., 9(3): 1082-1096 (1989).

Macor, J.E., et al., "The 5-$HT_3$ Antagonist Tropisetron (ICS 205-930) is a Potent and Selective α7 Nicotinic Receptor Partial Agonist," Bioorg. Med. Chem. Lett., 11: 319-321 (2001).

Malone, M.A., et al., "Hemispheric Processing and Methylphenidate Effects in Attention-Deficit Hyperactivity Disorder," J. Child Neurol., 9(2): 181-189 (1994).

Marks, M.J., et al., "Nicotinic Binding Sites in Rat and Mouse Brain: Comparison of Acetylcholine, Nicotine, and α-Bungarotoxin," Mol. Pharmacol., 30(5): 427-436 (1986).

Marks, M.J., et al., "Effects of Chronic Nicotine Infusion on Tolerence Development and Nicotinic Receptors," J. Pharmacol. Exp. Ther., 226(3): 817-825 (1983).

McConville, B.J., et al., "Nicotine Potentiation of Haloperidol in Reducing Tic Frequency in Tourette's Disorder," Am. J. Psychiatry, 148(6): 793-794 (1991).

McConville, B.J., et al., "The Effects of Nicotine Plus Haloperidol Compared to Nicotine Only and Placebo Nicotine Only in Reducing Tic Severity and Frequency in Tourette's Disorder," Biol. Psychiatry, 31(8): 832-840 (1992).

Merriam, A.E., et al., "Schizophrenia as a Neurobehavioral Disorder," Psychiatr. Annals, 23(4): 171-178 (1993).

Micouin, L., et al., "Asymmetric Synthesis. XXXIII. Diastereoselective Alkylation of N,N-substitued Amides," Tet. Lett., 35(39): 7223-7226 (1994).

Mitsunobu, O., "The Use of Diethyl Azodicarboxylate and Triphenylphoshine in Synthesis and Transformation of Natural Products," Synthesis, (1): 1-28 (1981).

Morisawa, Y., et al., "Studies on Anticoccidial Agents. 10. Synthesis and Anticoccidial Activity of 5-Nitronicothinamide and its Analogues," J. Med. Chem., 20(1): 129-133 (1977).

Newhouse, P.A., and J.R. Hughes, "The role of nicotine and nicotinic mechanisms in neuropsychiatric disease," Brit. J. Addic., 86: 521-525 (1991).

Nutaitis, C.F., and M.W. Ledeboer, "Preparation of Benzo[c-2,7]Naphthyridine," Org. Prep. And Proc. Int., 24(2): 143-146 (1992).

Olsen, S., and R. Bredoch, "Die Syntese des Oxa-cycloheptanons-(4) und des 4.4-Oxide-4-methyl-tetrahydropyrans," Chem. Ber., 91(7): 1589-1597 (1958).

O'Neill, M.J., et al., "The Role of Neuronal Nicotinic Acetylcholine Receptors in Acute and Chronic Neurodegeneration," Current Drug Targets: CNS and Neurological Disorders, 1(4): 399-411 (2002).

Onaivi, E.S., et al., "Chronic Nicotine Reverses Age-Associated Increases in Tail-Flick Latency and Anxiety in Rats," Life Sciences, 54(3): 193-202 (1994).

Oswald, R.E., et al., "Characterization of nicotinic acetylcholine receptor channels of the TE671 human medulloblastoma clonal line," Neurosci. Lett., 96(2): 207-212 (1989).

Perry, E.K., "The Cholinergic Hypothesis — Ten Years On," Br. Med. Bull., 42(1): 63-69 (1986).

Pomerleau, O.F., et al., "The Effects of Cigarette Smoking on Pain and Anxiety," Addictive Behaviors, 9: 265-271 (1984).

Pullan, R.D., et al. "Transdermal Nicotine for Active Ulcerative Colitis," New England J. Med., 330(12): 811-815 (1994).

Rapier, C., et al., "Stereoselective Nicotine-Induced Release of Dopamine from Striatal Synaptosomes: Concentration Dependence and Repetitive Stimulation," J. Neurochem., 50(4): 1123-1130 (1988).

Rapier, C., et al., "Nicotinic Modulation of [$^3$H]Dopamine Release from Striatal Synaptosomes: Pharmacological Characterisation," J. Neurochem., 54(3): 937-45 (1990).

Rinne, J.O., et al., "A postmortem study of brain nicotinic receptors in Parkinson's and Alzheimer's disease," Brain Res., 547(1): 167-170 (1991).

Romano, C., and A. Goldstein, "Stereospecific Nicotine Receptors on Rat Brain Membranes," Science, 210(7): 647-650 (1980).

Rowell, P.P. and D.L. Winkler, "Nicotinic Stimulation of [$^3$H] Acetylcholine Release from Mouse Cerebral Cortical Synaptosomes," J. Neurochem., 43(6): 1593-1598 (1984).

Rowell, P.P., "Current Concepts on the Effects of Nicotine on Neurotransmitter Release in the Central Nervous System," Adv. Behav. Biol., 31: 191-208 (1987).

Sahakian, B., et al., "The Effects of Nicotine on Attention, Information Processing, and Short-Term Memory in Patients with Dementia of the Alzheimer Type," Br. J. Psych., 154: 797-800 (1989).

Sanberg, P.R., and A.A. Silver, "Beneficial Effects of Nicotine in Tourette's Syndrome," *Proceedings for Intl. Symp. Nic.*, S39 (1994).

Sanberg, P.R., et al., "Nicotine Potentiation of Haloperidol-Induced Catalepsy: Striatal Mechanisms," *Pharmacol. Biochem. & Behavior*, 46: 303-307 (1993).

Sandor, N.T., et al. "Effect of nicotine on dopaminergic-cholinergic interaction in the striatum," *Brain Res.*, 567: 313-316 (1991).

Schmitt, J.D., and M. Bencherif, "Chapter 5. Targeting Nicotinic Acetylcholine Receptors: Advances in Molecular Design and Therapies," *Ann. Rep. Med. Chem.*, 35: 41-51 (2000).

Selnick, H.G., et al., "Preparation and Trapping of 3-Lithium-O-Lithiophenoxide," *Tet. Lett.*, 34(13): 2043-2046 (1993).

Sherwood, N., "Effects of Nicotine on Human Psychomotor Performance," *Human Psychopharm.*, 8: 155-184 (1993).

Sitaram, N., and H. Weingartner, "Human Serial Learning: Enhancement with Arecholine and Choline and Impairment with Scopolamine," *Science*, 201: 274-276 (1978).

Sjak-Shie, N.N., and E.M. Meyer, "Effects of chronic nicotine and pilocarpine administration on neocortocal neuronal density and [$^3$H]GABA uptake in nucleus basalis lesioned rats," *Brain Res.*, 624: 295-298 (1993).

Smith, C.J., and E. Giacobini, "Nicotine, Parkinson's and Alzheimer's Disease," *Rev. Neurosci.*, 3(1): 25-43 (1992).

Stevens, K.E., et al., "Selective α—nicotinic agonists normalize inhibition of auditory response in DBA mice," *Psychopharm.*, 136: 320-327 (1998).

Stratton, M.R., et al., "Characterization of the human cell line TE671," *Carcinogenesis*, 10(5): 899-905 (1989).

Suto, M.J., et al., "A New Class of Analogues of the Bifunctional Radiosensitizer α-(1-Aziridinylmethyl)-2- nitro-/H-imidazole-1-ethanol (RSU 1069): The Cycloalkylaziridines," *J. Med. Chem.*, 34(8): 2484-2488 (1991).

Thomas, J., and D. Clough, "The Preparation and Measurement of the Surface Activity of a Series of 4-Alkyl-1,1'-Spirobipiperidinium Bromides," *J. Pharm. Pharmacol.*, 15(3): 167-177 (1963).

Toth, E., et al., "Effect of Nicotine of Extracellular Levels of Neurotransmitters Assessed by Microdialysis in Various Brain Regions: Role of Glutamic Acid," *Neurochem. Res.*, 17(3): 265-270 (1992).

Tracey, K.J., "The Inflammatory Reflex," *Nature*, 420: 853-859 (2002).

Tripathi, H.L., et al., "Nicotine-Induced Antinociception of Rats and Mice: Correlation with Nicotine Brain Levels," *J. Pharmacol. Exp. Ther.*, 221(1): 91-96 (1982).

Villemagne, V.L., et al., "Nicotine and Related Compounds as PET and SPECT Ligands," *Neuronal Nicotinic Receptors: Pharmacology and Therapeutic Opportunities*, 235-250 (1999).

Vizi, E.S., "Acetylcholine release from quinea-pig ileum by parasympathetic ganglion stimulants and gastrin-like polypeptides," *Br. J. Pharmac.*, 47: 765-777 (1973).

Wagner, B., et al., "Does Smoking Reduce the Risk of Neuroleptic Parkinsonoids?" *Pharmacopsychiatry*, 21: 302-303 (1988).

Wang, H., et al., "Nicotinic acetylcholine receptor α-7 subunit is an essential regulator of inflammation," *Nature*, 421: 384-388 (2003).

Whiting, P.J., et al., "Expression of nicotinic acetylcholine receptor subtypes in brain and retina," *Brain Res. Mol. Brain Res.*, 10(1): 61-70 (1991).

Whiting, P.J., et al., "Functional acetylcholine receptor in PC12 cells reacts with a monoclonal antibody to brain nicotinic receptors," *Nature*, 327(6122): 515-518 (1987).

Williams, M., et al., "Neuronal Nicotinic Acetylcholine Receptors," *DN &P*, 7(4): 205-223 (1994).

Xiao, H., et al., "Identification of gene expression profile of dorsal root ganglion in the rat peripheral axotomy model of neuropathic pain," *Proc. Nat. Acad. Sci.*, 99(12): 8360-8365 (2002).

Zwart, C., and J.P. Wibaut, "Chemical Behavior of 3-Aminopyridine and of 3,5-Diaminopyridine. Syntheses of (3-Pyridyl)-Pyrazolones." *Recueil Trav. Chim. Pays-Bas*, 74(8/9): 1062-1069 (1955).

* cited by examiner

PHARMACEUTICAL COMPOSITIONS AND METHODS FOR EFFECTING DOPAMINE RELEASE

This application is a Continuation-in-Part of application Ser. No. 08/885,768 filed Jun. 30, 1997 (now U.S. Patent No. 6,624,173, issued Sep. 23, 2003).

FIELD OF THE INVENTION

The present invention relates to pharmaceutical compositions, particularly pharmaceutical compositions incorporating compounds that are capable of affecting nicotinic acetylcholinergic receptors (nAChRs). The present invention also relates to methods for treating a wide variety of conditions and disorders, particularly conditions and disorders associated with dysfunction of the central and autonomic nervous systems.

BACKGROUND OF THE INVENTION

Nicotine has been proposed to have a number of pharmacological effects. See, for example, Pullan et al., *N. Engl. J. Med.* 330:811 (1994). Certain of those effects may be related to effects upon neurotransmitter release. See for example, Sjak-shic et al., *Brain Res.* 624:295 (1993), where neuroprotective effects of nicotine are proposed. Release of acetylcholine and dopamine by neurons upon administration of nicotine has been reported by Rowell et al., *J. Neurochem.* 43:1593 (1984); Rapier et al., *J. Neurochem.* 50:1123 (1988); Sandor et al., *Brain Res.* 567:313 (1991) and Vizi, *Br. J. Pharmacol.* 47:765 (1973). Release of norepinephrine by neurons upon administration of nicotine has been reported by Hall et al., *Biochem. Pharmacol.* 21:1829 (1972). Release of scrotonin by neurons upon administration of nicotine has been reported by Hery et al., *Arch. Int. Pharmacodyn. Ther.* 296:91 (1977). Release of glutamate by neurons upon administration of nicotine has been reported by Toth et al., *Neurochem. Res.* 17:265 (1992). Confirmatory reports and additional recent studies have included the modulation, in the central nervous system (CNS), of glutamate, nitric oxide, GABA, takykinins, cytokines and peptides (reviewed in Brioni et al., *Adv. Pharmacol.* 37:153 (1997)). In addition, nicotine reportedly potentiates the pharmacological behavior of certain pharmaceutical compositions used for the treatment of certain CNS disorders. See Sanberg et al., *Pharmacol. Biochem. & Behavior* 46:303 (1993); Harsing et al., *J. Neurochem.* 59:48 (1993) and Hughes, *Proceedings from Intl. Symp. Nic.* S40 (1994). Furthermore, various other beneficial pharmacological effects of nicotine have been proposed. See, for example, Decina et al., *Biol. Psychiatry* 28:502 (1990); Wagner et al., *Pharmacopsychiatry* 21:301 (1988); Pomerleau et al., *Addictive Behaviors* 9:265 (1984); Onaivi et al., *Life Sci.* 54(3):193 (1994); Tripathi et al., *J. Pharmacol. Exp. Ther.* 221:91 (1982) and Hamon, *Trends in Pharmacol. Res.* 15:36.

Various nicotinic compounds have been reported as being useful for treating a wide variety of conditions and disorders. See, for example, Williams et al., *Drug News & Perspectives* 7(4):205 (1994); Arneric et al., *CNS Drug Rev.* 1(1):1 (1995); Arneric et al., *Exp. Opin. Invest. Drugs* 5(1):79 (1996); Bencherif et al., *J. Pharmacol. Exp. Ther.* 279:1413 (1996); Lippiello et al., *J. Pharmacol. Exp. Ther.* 279:1422 (1996); Damaj et al., *J. Pharmacol. Exp. Ther.* 291:390 (1999); Chiari et al., *Anesthesiology* 91:1447 (1999); Lavand'homme and Eisenbach, *Anesthesiology* 91:1455 (1999); Holladay et al., *J. Med. Chem.* 40(28): 4169 (1997); Bannon et al., *Science* 279: 77 (1998); PCT WO 94/08992, PCT WO 96/31475, and U.S. Pat. No. 5,583,140 to Bencherif et al., U.S. Pat. No. 5,597,919 to Dull et al., U.S. Pat. No. 5,604,231 to Smith et al. and U.S. Pat. No. 5,852,041 to Cosford et al. Nicotinic compounds are particularly useful for treating a wide variety of CNS disorders. Indeed, a wide variety of compounds have been reported to have therapeutic properties. See, for example, Bencherif and Schmitt, *Current Drug Targets: CNS and Neurological Disorders* 1(4): 349 (2002); Levin and Rezvani, *Current Drug Targets: CNS and Neurological Disorders* 1(4): 423 (2002); O'Neill et al., *Current Drug Targets: CNS and Neurological Disorders* 1(4): 399 (2002); U.S. Pat. No. 5,1871,166 to Kikuchi et al., U.S. Pat. No. 5,672,601 to Cignarella, PCT WO 99/21834 and PCT WO 97/40049, UK Patent Application GB 2295387 and European Patent Application 297,858.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of choline, dopamine, norepinephrine and/or serotonin. Relatively common CNS disorders include presenile dementia (early-onset Alzheimer's disease), senile dementia (dementia of the Alzheimer's type), micro-infarct dementia, AIDS-related dementia, Creutzfeld-Jakob disease, Pick's disease, Parkinsonism including Parkinson's disease, Lewy body dementia, progressive supranuclear palsy, Huntington's chorea, tardive dyskinesia, hyperkinesia, mania, attention deficit disorder, anxiety, dyslexia, schizophrenia, depression, obsessive-compulsive disorders and Tourette's syndrome.

Senile dementia of the Alzheimer's type (SDAT) is a debilitating neurodegenerative disease, mainly afflicting the elderly, characterized by a progressive intellectual and personality decline, as well as a loss of memory, perception, reasoning, orientation and judgment. One feature of the disease is an observed decline in the function of cholinergic systems, and specifically, a severe depletion of cholinergic neurons (i.e., neurons that release acetylcholine, which is believed to be a neurotransmitter involved in learning and memory mechanisms). See, for example, Jones et al., *Intern. J. Neurosci.* 50:147 (1990); Perry, *Br. Med. Bull.* 42:63 (1986); and Sitaram et al., *Science* 201:274 (1978). It has been observed that nicotinic acetylcholine receptors, which bind nicotine and other nicotinic agonists with high affinity, are depleted during the progression of SDAT. See Giacobini, *J. Neurosci. Res.* 27:548 (1990) and Baron, *Neurology* 36:1490 (1986). As such, it would seem desirable to provide therapeutic compounds that either directly activate nicotinic receptors in place of acetylcholine or act to minimize the loss of those nicotinic receptors.

Certain attempts have been made to treat SDAT. For example, nicotine has been suggested to possess an ability to activate nicotinic cholinergic receptors upon acute administration and to elicit an increase in the number of such receptors upon chronic administration to animals. See, for example, Rowell, *Adv. Behav. Biol.* 31:191 (1987) and Marks, *J. Pharmacol. Exp. Ther.* 226:817 (1983). It also has been proposed that nicotine can act directly to elicit the release of acetylcholine in brain tissue, to improve cognitive functions, and to enhance attention. See Rowell et al., *J. Neurochem.* 43:1593 (1984); Sherwood, *Human Psychopharm.* 8:155 (1993); Hodges et al., *Bio. of Nic.* Edit. by Lippiello et al., p. 157 (1991); Sahakian et al., *Br. J. Psych.* 154:797 (1989); and U.S. Pat. No. 4,965,074 to Leeson and U.S. Pat. No. 5,242,935 to Lippiello et al. Other methods for treating SDAT have been proposed, including U.S. Pat. No. 5,212,188 to Caldwell et al. and U.S. Pat. No. 5,227,391 to Caldwell et al., European Patent Application No. 588,917 and PCT WO 96/30372. Another proposed treatment for SDAT is COGNEX®, which is a capsule containing tacrine hydrochloride, available from Parke-Davis Division of Warner-Lambert Company, which reportedly preserves existing acetylcholine levels in patients treated therewith.

Parkinson's disease (PD) is a debilitating neurodegenerative disease, presently of unknown etiology, characterized by tremors and muscular rigidity. A feature of the disease appears to involve the degeneration of dopaminergic neurons (i.e., which secrete dopamine). One symptom of the disease has been observed to be a concomitant loss of nicotinic receptors which are associated with such dopaminergic neurons, and which are believed to modulate the process of dopamine secretion. See Rinne et al., *Brain Res.* 54:167 (1991) and Clark et al., *Br. J. Pharm.* 85:827 (1985). It also has been proposed that nicotine can ameliorate the symptoms of PD, as discussed in Smith et al., *Rev. Neurosci.* 3(1):25 (1992).

Certain attempts have been made to treat PD. One proposed treatment for PD is SINEMET CR®, which is a sustained-release tablet containing a mixture of carbidopa and levodopa, available from The DuPont Merck Pharmaceutical Co. Another proposed treatment for PD is ELDEPRYL®, which is a tablet containing selefiline hydrochloride, available from Somerset Pharmaceuticals, Inc. Another proposed treatment for PD is PARLODEL®, which is a tablet containing bromocriptine mesylate, available from Sandoz Pharmaceuticals Corporation. Another method for treating PD and a variety of other neurodegenerative diseases has been proposed in U.S. Pat. No. 5,210,076 to Berliner et al.

Tourette's syndrome (TS) is an autosomal dominant neuropsychiatric disorder characterized by a range of neurological and behavioral symptoms. Typical symptoms include (i) the onset of the disorder before the age of 21 years, (ii) multiple motor and phonic tics although not necessarily concurrently, (iii) variance in the clinical phenomenology of the tics, and (iv) occurrence of quasi-daily tics throughout a period of time exceeding a year. Motor tics generally include eye blinking, head jerking, shoulder shrugging and facial grimacing; while phonic or vocal tics include throat clearing, sniffling, yelping, tongue clicking and uttering words out of context. The pathophysiology of TS presently is unknown, however it is believed that neurotransmission dysfunction is implicated with the disorder. For further discussion, see Calderon-Gonzalez et al., *Intern. Pediat.* 8(2):176 (1993) and *Oxford Textbook of Medicine*, Weatherall et al., eds., p.218 (1987).

It has been proposed that nicotine pharmacology is beneficial in suppressing the symptoms associated with TS. See Devor et al., *The Lancet* 8670: 1046 (1989); Jarvik, *Brit. J. of Addic.* 86: 571 (1991); McConville et al., *Am. J. Psychiatry* 148(6): 793 (1991); Newhouse et al., *Brit. J. Addic.* 86: 521 (1991); McConville et al., *Biol. Psychiatry* 31: 832 (1992); and Sanberg et al., *Proceedings from Intl. Symp. Nic.* S39 (1994). It also has been proposed to treat TS using HIALDOL®, which is haloperidol available from McNeil Pharmaceutical; CATAPRES®, which is clonidine available from Boehringer Ingelheim Pharmaceuticals, Inc., ORAP®, which is pimozide available from Gate Pharmaceuticals; PROLIXIN®, which is fluphenazine available from Apothecon Division of Bristol-Myers Squibb Co.; and KLONOPIN®, which is clonazepam available from Hofformann-LaRoche Inc.

Attention deficit disorder (ADD) is a disorder that affects mainly children, although ADD can affect adolescents and adults. See Vinson, *Arch. Fam. Med.* 3(5): 445 (1994); Hechtman, *J. Psychiatry Neurosci.* 19(3): 193 (1994); Faraone et al., *Biol. Psychiatry* 35(6): 398 (1994) and Malone et al., *J. Child Neurol.* 9(2): 181 (1994). Subjects suffering from the disorder typically have difficulty concentrating, listening, learning and completing tasks; and are restless, fidgety, impulsive and easily distracted. Attention deficit disorder with hyperactivity (ADHD) includes the symptoms of ADD as well as a high level of activity (e.g., restlessness and movement). Attempts to treat ADD have involved administration of DEXEDRINE®, which is a sustained release capsule containing dextroamphetamine sulfate, available from SmithKline Beecham Pharmaceuticals; RITALIN®, which is a tablet containing methylphenidate hydrochloride, available from Ciba Pharmaceutical Company; and CYLERT®, which is a tablet containing premoline, available from Abbott Laboratories. In addition, it has been reported that administration of nicotine to an individual improves that individual's selective and sustained attention. See Warburton et al., *Cholinergic Control of Cognitive Resources, Europsychobiology*, Mendlewicz et al., eds., p. 43 (1993) and Levin et al., *Psychopharmacology* 123:55 (1996).

Schizophrenia is characterized by psychotic symptoms including delusions, catatonic behavior and prominent hallucinations, and ultimately results in a profound decline in the psychosocial affect of the subject suffering therefrom. Traditionally, schizophrenia has been treated with KLONOPIN®, which is available as a tablet containing clonezepam, available from Hoffmann-LaRoche Inc.; THORAZINE®, which is available as a tablet containing chlorpromazine, available from SmithKline Beecham Pharmaceuticals; and CLORAZIL®, which is a tablet containing clozapine, available from Sandoz Pharmaceuticals. Such neuroleptics are believed to be effective as a result of interaction with the dopaminergic pathways of the CNS. In addition, a dopaminergic dysfunction possessed by individuals suffering from schizophrenia has been proposed. See Lieberman et al., *Schizophr. Bull.* 19:371 (1993) and Glassman, *Amer. J. Psychiatry* 150:546 (1993). Nicotine has been proposed to be effective in modulating neurotransmitter dysfunction associated with schizophrenia. See Merriam et al., *Psychiatr. Annals* 23:171 (1993) and Adler et al., *Biol. Psychiatry* 32:607 (1992). See also Freedman et al., *Proc. Natl. Acad. Sci.* 94:587 (1997).

It would be desirable to provide a useful method for the prevention and treatment of a condition or disorder by administering a nicotinic compound to a patient susceptible to or suffering from such a condition or disorder. It would be highly beneficial to provide individuals suffering from certain disorders (e.g., CNS diseases) with interruption of the symptoms of those disorders by the administration of a pharmaceutical composition containing an active ingredient having nicotinic pharmacology which has a beneficial effect (e.g., upon the functioning of the CNS), but does not provide any significant associated side effects. It would be highly desirable to provide a pharmaceutical composition incorporating a compound that interacts with nicotinic receptors, such as those that have the potential to affect the functioning of the CNS. The present invention provides such compounds, compositions and methods.

There exist subtypes of nAChRs in both the central and peripheral nervous systems, but the distribution of subtypes is heterogeneous. For instance, the subtypes which are predominant in vertebrate brain are α4β2, α7, and α3β2, whereas those which predominate at the autonomic ganglia are α3β4 and those of neuromuscular junction are α1β1δγ and α1β1δε (see for instance Dwoskin et al., *Exp. Opin. Ther. Patents* 10: 1561 (2000) and Schmitt and Biencherif, *Annual Reports in Med. Chem.* 35: 41 (2000)). A limitation of some nicotinic compounds is that they elicit various undesirable pharmacological effects because of their interaction with nAChRs in peripheral tissues (for example, by stimulating muscle and ganglionic nAChR subtypes). It would be desirable to have compounds, compositions and methods for preventing and/or treating various conditions or disorders (e.g., CNS disorders), including alleviating the symptoms of these disorders, where the compounds exhibit nicotinic pharmacology with a beneficial effect on the CNS nAChRs (e.g., upon the functioning of the CNS), but without significant associated effects on the peripheral nAChRs (compounds specific for CNS nAChRs, without significant effects on cardiovascular and/or skeletal muscle receptor sites). The present invention provides such compounds, compositions and methods.

SUMMARY OF THE INVENTION

Methods for preventing and/or treating disorders, such as CNS disorders, characterized by an alteration in normal neurotransmitter release, such as dopamine release, are disclosed. The methods involve administering to a subject an effective amount of an 2-(3-pyridyl)-1-azabicyclo[2.2.1]heptane, a 2-(3-pyridyl)-1-azabicyclo[2.2.2] octane, a 2-(3-pyridyl)-1-azabicyclo[3.2.1]octane, a 2-(3-pyridyl)-1-azabicyclo[3.2.2]nonane, a 7-(3-pyridyl)-1-azabicyclo[2.2.1] heptane, a 3-(3-pyridyl)-1-azabicyclo[3.2.2]nonane, or a 7-(3-pyridyl)-1-azabicyclo[3.2.2]nonane, including enantiomerially enriched forms thereof. Also disclosed are compounds useful in the methods, and pharmaceutical compositions comprising an effective amount of these compounds. The compositions incorporate a compound which, when employed in effective amounts, has the capability of interacting with relevant nicotinic receptor sites of a subject, and hence has the capability of acting as a therapeutic agent in the prevention or treatment of disorders characterized by an alteration in normal neurotransmitter release. Preferred pharmaceutical compositions comprise novel compounds of the present invention.

The pharmaceutical compositions are useful for preventing and/or treating disorders, such as CNS disorders, which are characterized by an alteration in normal neurotransmitter release. The pharmaceutical compositions provide therapeutic benefit to individuals suffering from such disorders and exhibiting clinical manifestations of such disorders. The compounds, administered with the pharmaceutical compositions, can be employed in effective amounts to (i) exhibit nicotinic pharmacology and affect relevant nicotinic receptors sites (e.g., act as a pharmacological agonists at nicotinic receptors), and (ii) modulate neurotransmitter secretion, and hence prevent and suppress the symptoms associated with those diseases. In addition, the compounds have the potential to (i) increase the number of nicotinic cholinergic receptors of the brain of the patient, (ii) exhibit neuroprotective effects and (iii) when employed in effective amounts, not cause appreciable adverse side effects (e.g., significant increases in blood pressure and heart rate, significant negative effects upon the gastro-intestinal tract, and significant effects upon skeletal muscle). The pharmaceutical compositions are believed to be safe and effective with regards to prevention and treatment of various conditions or disorders.

The foregoing and other aspects of the present invention are explained in detail in the detailed description and examples set forth below.

DETAILED DESCRIPTION OF THE INVENTION

The compounds, compositions and methods described herein will be better understood with reference to the following preferred embodiments. The following definitions will be useful in defining the scope of the invention:

As used herein, "aromatic" refers to 3 to 10, preferably 5 and 6-membered ring aromatic and heteroaromatic rings.

As used herein, "aromatic group-containing species" refer to moieties that are or include an aromatic group. Accordingly, phenyl and benzyl moieties are included in this definition, as both are or include an aromatic group.

As used herein, $C_{1-6}$ alkyl radicals (lower alkyl radicals) contain from 1 to 6 carbon atoms in a straight or branched chain, and also include $C_{3-6}$ cycloalkyl moieties and alkyl radicals that contain $C_{3-6}$ cycloalkyl moieties.

As used herein, $C_{1-6}$ alkoxy radicals contain from 1 to 6 carbon atoms in a straight or branched chain, and also include $C_{3-6}$ cycloalkyl and alkoxy radicals that contain $C_{3-6}$ cycloalkyl moieties.

As used herein, aryl radicals are selected from phenyl, naphthyl and indenyl.

As used herein, heteroaryl radicals contain from 3 to 10 members, preferably 5 or 6 members, including one or more heteroatoms selected from oxygen, sulfur and nitrogen. Examples of suitable 5 membered ring heteroaryl moieties include furyl, thienyl, pyrrolyl, imidazolyl, oxazolyl, thiazolyl, tetrazolyl, and pyrazolyl. Examples of suitable 6 membered ring heteroaryl moieties include pyridyl, pyrimidinyl, pyrazinyl, of which pyridyl and pyrimidinyl are preferred.

As used herein, halogen is chlorine, iodine, fluorine or bromine.

As used herein, polycycloalkyl radicals are fused cyclic ring structures. Representative polycycloalkyl radicals include, but are not limited to, adamantyl, bornanyl, norbornanyl, bornenyl and norbornenyl. Polycycloalkyl radicals can also include one or more heteroatoms, such as N, O or S.

As used herein, heterocyclyl radicals contain from 3 to 10 members including one or more heteroatoms selected from oxygen, sulfur and nitrogen. Examples of suitable heterocyclyl moieties include, but are not limited to, piperidinyl, morpholinyl, pyrrolidinyl, imidazolidinyl, pyrazolidinyl, isothiazolidinyl, thiazolidinyl, isoxazolidinyl, oxazolidinyl, piperazinyl, oxanyl (tetrahydropyranyl) and oxolanyl (tetrahydrofuranyl).

As used herein, cycloalkyl radicals contain from 3 to 8 carbon atoms. Examples of suitable cycloalkyl radicals include, but are not limited to, cyclopropyl, cyclobutyl, cyclopentyl, cyclohexyl, cycloheptyl and cyclooctyl.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates. Representative salts are provided as described in U.S. Pat. No. 5,597,919 to Dull et al., U.S. Pat. No. 5,616,716 to Dull et al. and U.S. Pat. No. 5,663,356 to Ruecroft et al.

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" is a substance that provides a level of stimulation to its binding partner that is intermediate between that of a full or complete antagonist and an agonist defined by any accepted standard for agonist activity. It will be recognized that stimulation, and hence, inhibition is defined intrinsically for any substance or category of substances to be defined as agonists, antagonists, or partial agonists. As used herein, "intrinsic activity", or "efficacy," relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. See Hoyer and Boddeke, Trends Pharmacol Sci. 14(7): 270 (1993). Where such contextually specific evaluations are relevant, and how they might be relevant in the context of the present invention, will be apparent to one of ordinary skill in the art.

As used herein, neurotransmitters whose release is mediated by the compounds described herein include, but are not limited to, acetylcholine, dopamine, norepinephrine, serotonin and glutamate, and the compounds described herein function as agonists or partial agonists at one or more of the CNS nAChRs.

I. Compounds

The present invention relates to compounds having the general Formula I:

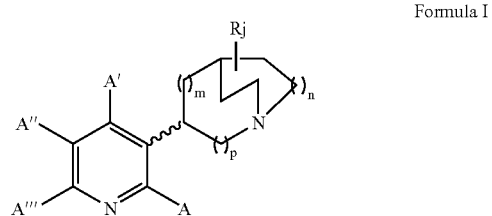

Formula I where A, A', A" and A'" are individually substituent species characterized as having a sigma m value greater than 0, often greater than 0.1, and generally greater than 0.2, and even greater than 0.3; less than 0, generally less than −0.1; or 0; as determined in accordance with Hansch et al., Chem. Rev. 91:165 (1991); m, n and p are individually 0, 1 or 2, and the sum of p plus m is equal to 1 or 2 when n=0; R is a substituent other than hydrogen, and can otherwise be selected from the same group of substituents as A, A', A" and A'"; j is an integer from 0 to 5, preferably 0 or 1, and most preferably 0; and the wavy line in the structure indicates that, depending upon the values of each of n, m, and p, the stereochemistry of the carbon at which the azabicyclic ring is attached to the pyridine ring can be either R or S, and the compound can be either the exo or endo diastereomer. The sum of m plus n plus p can vary, and typically is an integer from 1 to 4, with a sum of 1 to 3 being preferred. The identity of A, A', A" and A'" can vary, and each of those substituent species often has a sigma m value between about −0.3 and about 0.75, frequently between about −0.25 and about 0.6. More specifically, examples of A, A', A" and A'" include —H, —F, —Cl, —Br, —I, —R', —NR'R", —CF$_3$, —CN, —NO$_2$, —C$_2$R', —SCH$_3$, —N$_3$, —SO$_2$CH$_3$, —OR', —SR', —C(=O)NR'R", —NR'C(=O)R', —C(=O)R', —C(=O)OR', —(CH$_2$)$_q$OR', —OC(=O)R', —OC(=O)NR'R", and —NR'C(=O)OR', where R' and R" are individually hydrogen or lower alkyl (e.g., C$_1$, —C$_{10}$ alkyl, preferably C$_1$–C$_6$ alkyl, and more preferably methyl, ethyl, isopropyl or isobutyl) or an aromatic group-containing species, and q is an integer from 1 to 6.

Representative aromatic group-containing species include pyridyl (pyridinyl), quinolinyl, pyrimidinyl, phenyl, and benzyl (where any of the foregoing can be suitably substituted with at least one substituent group, such as alkyl, halo, or amino substituents). Representative aromatic ring systems are set forth in Gibson et al., J. Med. Chem. 39: 4065 (1996).

For NR'R", the nitrogen and R' and R" can combine to form a ring structure, such as aziridinyl, azetidinyl, pyrrolidinyl, piperidinyl, piperazinyl or morpholinyl. Typically, R is positioned at a carbon bridgehead of the azabicyclo moiety, at a carbon adjacent to the carbon or nitrogen bridgehead of the azabicyclo moiety, or at the carbon adjacent to the carbon bearing the pyridyl substituent.

The compounds represented in Formula I can be optically active. Isomers, mixtures, including racemic mixtures, enantiomers, diastereomers and tautomers of these compounds, as well as pharmaceutically acceptable salts thereof, are also intended to be within the scope of the present invention.

In certain circumstances, it is preferred that the sigma m value of A" is not equal to 0. In addition, it is highly preferred that A is hydrogen, it is preferred that A' is hydrogen, and normally A'" is hydrogen. Generally, both A and A' are hydrogen; sometimes A and A' are hydrogen, and A'" is halo, —OR', —OH, —NR'R", —SH or —SR'; and often A, A' and A'" are all hydrogen. For certain preferred compounds, A" is a non-hydrogen substituent (i.e., such compounds are 5-substituted-3-pyridyl compounds).

Representative compounds include 2-(3-pyridyl)-1-azabicyclo[2.2.1]heptanes, which can exist in various stereoisomeric forms, and for which n=0, m=1 and p=0; 2-(3-pyridyl)-1-azabicyclo[2.2.2]octanes, for which n=1, m=1 and p=0; 2-(3-pyridyl)-1-azabicyclo[3.2.2]nonanes, for which n=1, m=2 and p=0; 7-(3-pyridyl)-1-azabicyclo[2.2.1]heptanes, for which n=1, m=0 and p=0; 3-(3-pyridyl)-1-azabicyclo[3.2.2]nonanes, for which n=1, m=1 and p=1; and 7-(3-pyridyl)-1-azabicyclo[3.2.2]nonanes, for which n=2, m=1 and p=0. Each of the representative compounds can exist in various stereoisomeric forms.

II. Methods of Preparing the Compounds

The manner in which compounds of the present invention can be synthesized can vary. In one approach, illustrated in Schemes 1 and 2 below, a suitable pyridine-containing nucleophile can be reacted with a suitable cyclic ether-containing alkylating agent (B). The resulting intermediates can then be converted into compounds of the present invention. In Scheme 1, a process for making compounds in which p=0 is outlined. In this case, the pyridine-containing nucleophile is the carbanion derived from an imine (A) and lithium diisopropylamide. The imine is, in turn, formed from commercially available 3-(aminomethyl)pyridine and benzophenone. Such alkylation reactions can be performed in a stereospecific manner by utilizing using imines formed from 2-hydroxy-3-pinanone, as described by Chen et al., *Synth. Comm.* 19: 1423 (1989). Hydrolysis of the alkylated imine gives amine C, which can be transformed, by sequential treatment with hydrobromic acid and potassium carbonate, into product D. 2-(3-Pyridyl)-1-azabicyclo[2.2.1]heptane, 2-(3-pyridyl)-1-azabicyclo[2.2.2]octane, 2-(3-pyridyl)-1-azabicyclo[3.2.2]nonane, 7-(3-pyridyl)-1-azabicyclo[2.2.1]heptane, 8-(3-pyridyl)-1-azabicyclo[3.2.1]octane and 7-(3-pyridyl)-1-azabicyclo[3.2.2]nonane can each be made using the appropriate alkylating agent (B) in Scheme 1.

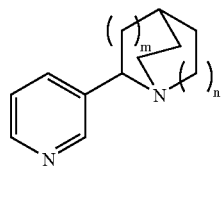

D

In a method complementary to that outlined in Scheme 1, imines derived from 3-acetylpyridine can be used in alkylation reactions, as described by De Kimpe et al., *Tet. Lett.* 34: 4693 (1993). Thus, when the imine, formed from isopropylamine and 3-acetylpyridine, is treated sequentially with lithium diisopropylamide and 4-(bromomethyl)oxane, 1-(3-pyridyl)-3-(4-oxanyl)propan-1-one is formed. Reductive amination of this ketone produces C (m=2, n=1). Using 3-(bromomethyl)oxolane, instead of 4-(bromomethyl)oxane, in the same sequence of reactions, gives C, in which m=2 and n=0. The use of other alkylating agents will result in the production of the corresponding amines (C).

A process for making compounds in which p=1 is outlined in Scheme 2. In this case, the pyridine-containing nucleophile is the carbanion made from a suitable derivative of 3-pyridylacetic acid (such as ester E) and lithium diisopropylamide. Alkylation product F can be transformed into amine G by various procedures. For instance, treatment of the ester with ammonia will produce the corresponding amide, which can then be reduced using lithium aluminum hydride to give the amine. Amine G can be converted, by sequential treatment with hydrobromic acid and potassium carbonate, into product H. Compounds such as 3-(3-pyridyl)-1-azabicyclo[3.2.1]octane and 3-(3-pyridyl)-1-azabicyclo[3.2.2]nonane can be made by such methods.

Scheme 1

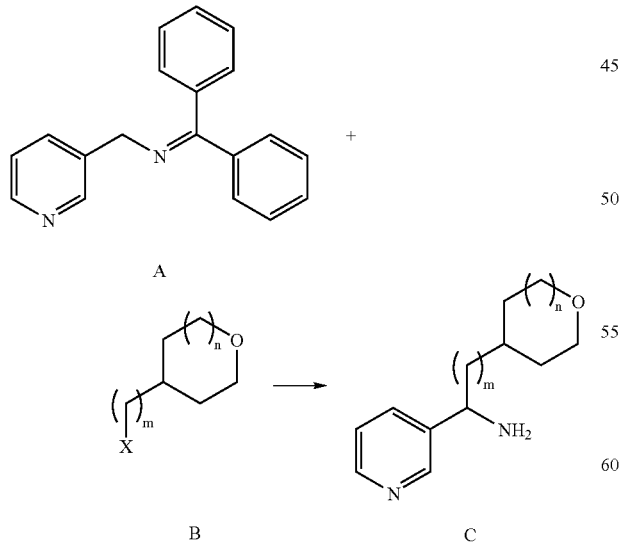

Scheme 2

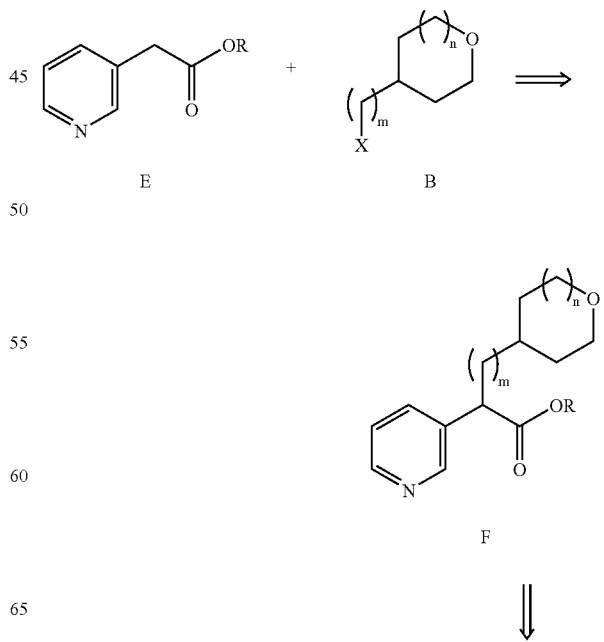

-continued

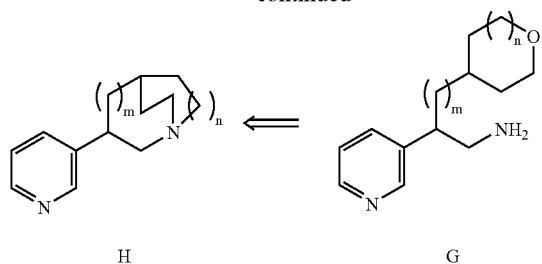

H    G

In a modification of this approach, various amide derivatives of E can be used in the alkylation reaction, using techniques well known to those skilled in the art of organic synthesis. In some cases these amides are useful in performing stereospecific alkylations. One such protocol is described by Micouin, *Tet. Lett.* 35: 7223 (1994).

The manner in which the alkylating agents (B), used in Schemes 1 and 2, can be made can vary. Commercially available oxolane-3-methanol can be converted into its methanesulfonate ester and subsequently into various alkyl halides, using methods known to those skilled in the art. Either the methanesulfonate or the alkyl halides can be used in the above outlined alkylation reactions to make compounds of the present invention in which m=1 and n=0. Using the same reactions, other cyclic ethers with hydroxy or hydroxyalkyl substituents can be converted into compounds of the present invention. For example, oxan-4-ol (from the hydride reduction of commercially available oxan-4-one) can be converted into compounds in which n=0 and n=1. In another example, oxane-4-methanol can be converted into compounds in which m=1 and n=1. The synthesis of oxane-4-methanol is reported by Burger et al., *J. Amer. Chem. Soc.* 72: 5512 (1950). 2-(4-Oxanyl)ethanol can be converted into compounds in which m=2 and n=1, 2-(4-Oxanyl)ethanol can be made from oxan-4-one by reaction with triethyl phosphonoacetate, followed by sequential reduction of the double bond (by hydrogenation) and the ester (by lithium aluminum hydride). 2-(3-Oxolanyl)ethanol can be converted into compounds in which m=2 and n=0. 2-(3-Oxolanyl)ethanol can be made by catalytic reduction of triethyl citrate (as described in German patent DE 4233430) or by lithium aluminum hydride reduction of the triethyl ester of tricarballylic acid (as described by Moore, *Org. Prep. Proced. Int.* 3: 213 (1971)). Oxepan-4-ol, prepared as described by Olsen, *Chem. Ber.* 91: 1589 (1958), can be converted into compounds in which m=0 and n=2. 4-(Hydroxymethyl)oxepane can be converted into compounds in which in m=1 and n=2, and can be produced from oxepan-4-one by various synthetic routes. In one route, oxepan-4-one can be treated sequentially with methylenetriphenylphosphorane (to make the exocyclic alkene) and diborane, followed by hydrogen peroxide (to hydrate the alkene). In another reaction sequence, oxepan-4-one can be treated with methoxymethylenetriphenylphosphorane, to make the exocyclic vinyl ether. Hydrolysis of the vinyl ether in mild acid, followed by reduction of the resulting aldehyde, produces 4-(hydroxymethyl)oxepane. The synthesis of oxepan-4-one is also described by Olsen, *Chem. Ber.* 91: 1589 (1958).

Some of the alkylating agents (B) contain an asymmetrically substituted carbon atom. Alkylation reactions between these chiral alkylating agents and nucleophiles, derived from compounds like A and E, will produce diastereomeric products. Typically the diastereomers can be separated from one another by chromatography or crystallization. In the cases in which the alkylation reaction proceeds in a stereospecific fashion (e.g., by using techniques such as those described elsewhere in this section), the separation of the diastereomeric products will provide enantiomerically pure materials.

The manner in which certain 5-substituted-3-pyridyl compounds of the present invention can be synthetically produced can vary. For example, 5-bromo-3-pyridyl compounds can be prepared using a combination of synthetic techniques known in the art. 5-Bromo-substituted analogs of 2-(3-pyridyl)-1-azabicyclo[2.2.1]heptane, 2-(3-pyridyl)-1-azabicyclo[2.2.2]octane, 2-(3-pyridyl)-1-azabicyclo[3.2.2]nonane, 7-(3-pyridyl)-1-azabicyclo[2.2.1]heptane, 8-(3-pyridyl)-1-azabicyclo[3.2.1]octane and 7-(3-pyridyl)-1-azabicyclo[3.2.2]nonane can all be prepared using synthetic methodology outlined in Scheme 1 and the corresponding 5-bromo intermediates. 5-Bromonicotinic acid, which is commercially available from Aldrich, is a convenient starting material for the synthesis of 5-bromo-3-(aminomethyl)pyridine, which is the precursor of the 5-bromo analog of A. The 5-bromonicotinic acid is converted to the mixed anhydride with ethyl chloroformate and reduced with lithium aluminum hydride in tetrahydrofuran at −78° C., to afford 5-bromo-3-(hydroxymethyl)pyridine, as reported by Ashimori et al., *Chem. Pharm. Bull.* 38:2446 (1990). Alternatively, the 5-bromonicotinic acid is esterified in the presence of sulfuric acid and ethanol, and then the intermediate ester is reduced with sodium borohydride to yield 5-bromo-3-(hydroxymethyl)pyridine, according to the techniques reported in Natatis et al., *Org. Prep. and Proc. Int.* 24:143 (1992). The resulting 5-bromo-3-(hydroxymethyl)pyridine can then be converted to the 5-bromo-3-(aminomethyl)pyridine utilizing a modification of the techniques of Mitsunobu, *Synthesis* 1 (1981), or via treatment of 5-bromo-3-(hydroxymethyl)pyridine with thionyl chloride and reaction of the resulting 5-bromo-3-(chloromethyl)pyridine hydrochloride with aqueous ammonia/ethanol, according to North et al., WO 95/28400. 5-Bromo-3-(aminomethyl)pyridine can be converted to 3-(1-azabicyclo[2.2.2]oct-2-yl)-5-bromopyridine using methods described in U.S. Pat. No. 5,510,355 to Bencherif et al., the disclosures of which are hereby incorporated by reference in its entirety.

The manner in which the 5-bromo-3-pyridyl analogs 3-(3-pyridyl)-1-azabicyclo[3.2.1]octane and 3-(3-pyridyl)-1-azabicyclo[3.2.2]nonane can be prepared is analogous to the synthesis of the unsubstituted compounds reported above (Scheme 2). Thus the ethyl ester of commercially available 5-bromo-3-pyridyl acetic acid is converted into its enolate by reaction with lithium diisopropylamide. The enolate nucleophile is then reacted with the desired alkylating agent, to produce various 5-bromo derivatives of F. Subsequent conversion to the amide (ethanolic ammonia) and reduction (borane) gives the 5-bromo derivative of G, which can then be cyclized to H.

A number of compounds possessing substituents at the 5-position of the pyridine ring can be prepared from the corresponding 5-bromo compound. For example, the 5-amino-substituted compound can be prepared from the corresponding 5-bromo compound, using ammonia in the presence of a copper catalyst according to the general method of Zwart et al., *Recueil Trav. Chim. Pays-Bas* 74: 1062 (1955). 5-Alkylamino-substituted compounds can be prepared in a similar manner. 5-Alkoxy-substituted analogs can be prepared from the corresponding 5-bromo compounds by heating with a sodium alkoxide in N,N-dimethylformamide or by use of a copper catalyst according to the general techniques described by Comins et al., *J. Org. Chem.* 55: 69 (1990) and den Hertog et al., *Recueil Trav. Chim. Pays-Bas* 74: 1171 (1955). 5-Ethynyl-substituted compounds can be prepared from the appropriate 5-bromo compounds by palladium-catalyzed coupling using 2-methyl-3-butyn-2-ol, followed by base (sodium hydride) catalyzed deprotection, according to the general techniques described by Cosford et al., *J. Med. Chem.* 39: 3235 (1996). The 5-ethynyl analogs can be converted into the corresponding 5-ethenyl, and subsequently to the corresponding 5-ethyl analogs by successive catalytic hydrogenation reactions. The 5-phenyl analogs can be prepared from the 5-bromo compounds by Suzuki coupling with phenylboronic acid. Substituted phenylboronic acids can also be used. The 5-azido-substituted analogs can be prepared from the corresponding 5-bromo compounds by reaction with sodium azide in N,N-dimethylformamide. 5-Alkylthio-substituted analogs can be prepared from the corresponding 5-bromo compound by reaction with an appropriate alkylmercaptan in the presence of sodium, using techniques known to those skilled in the art of organic synthesis.

A number of 5-substituted analogs of the aforementioned compounds can be synthesized from the corresponding 5-amino compounds via the 5-diazonium salt intermediates. Among the other 5-substituted analogs that can be produced from 5-diazonium salt intermediates are: 5-hydroxy analogs, 5-alkoxy analogs, 5-fluoro analogs, 5-chloro analogs, 5-bromo analogs, 5-iodo analogs, 5-cyano analogs and 5-mercapto analogs. These compounds can be synthesized using the general techniques set forth in Zwart et al., *Recueil Trav. Chim. Pay-Bas* 74: 1062 (1955). For example, 5-hydroxy-substituted analogs can be prepared from the reaction of the corresponding 5-diazonium salt intermediates with water. 5-Alkoxy analogs can be prepared by reaction of the diazonium salts with alcohols. 5-Fluoro-substituted analogs can be prepared from the reaction of the 5-diazonium salt intermediates with fluoroboric acid. 5-Chloro-substituted analogs can be prepared from the reaction of the 5-amino compounds with sodium nitrite and hydrochloric acid in the presence of copper chloride. 5-Cyano-substituted analogs can be prepared from the reaction of the corresponding 5-diazonium salt intermediates with potassium copper cyanide. Appropriate 5-diazonium salt intermediates can also be used for the synthesis of mercapto-substituted analogs using the general techniques described in Hoffman et al., *J. Med. Chem.* 36: 953 (1993). The 5-mercapto-substituted analogs can in turn be converted to the 5-alkylthio-substituted analogs by reaction with sodium hydride and an appropriate alkyl bromide. 5-Amino-substituted analogs can also be converted to the corresponding 5-nitro analogs by reaction with fuming sulfuric acid and peroxide, according to the general techniques described in Morisawa, *J. Med. Chem.* 20: 129 (1977) for converting an aminopyridine to a nitropyridine. 5-Acylamido analogs of the aforementioned compounds can be prepared by reaction of the corresponding 5-amino compounds with an appropriate acid anhydride or acid chloride, using techniques known to those skilled in the art of organic synthesis.

5-Hydroxy-substituted analogs of the aforementioned compounds can be used to prepare corresponding 5-alkanoyloxy-substituted compounds by reaction with the appropriate acid, acid chloride, or acid anhydride. Likewise, the 5-hydroxy compounds are precursors of both the 5-aryloxy and 5-heteroaryloxy analogs via nucleophilic aromatic substitution at electron deficient aromatic rings (e.g., 4-fluorobenzonitrile and 2,4-dichloropyrimidine). Such chemistry is well known to those skilled in the art of organic synthesis. Ether derivatives can also be prepared from the 5-hydroxy compounds by alkylation with alkyl halides and a suitable base or via Mitsunobu chemistry, in which a trialkyl- or triarylphosphine and diethyl azodicarboxylate are typically used. See Hughes, *Org. React.* (N.Y.) 42: 335 (1992) and Hughes, *Org. Prep. Proced. Int.* 28: 127 (1996) for typical Mitsunobu conditions.

5-Cyano-substituted analogs of the aforementioned compounds can be hydrolyzed to afford the corresponding 5-carboxamido-substituted compounds. Further hydrolysis results in formation of the corresponding 5-carboxylic acid-substituted analogs. Reduction of the 5-cyano-substituted analogs with lithium aluminum hydride yields the corresponding 5-aminomethyl analogs. 5-Acyl-substituted analogs can be prepared from corresponding 5-carboxylic acid-substituted analogs by reaction with an appropriate alkyllithium reagent using techniques known to those skilled in the art of organic synthesis.

5-Carboxylic acid-substituted analogs of the aforementioned compounds can be converted to the corresponding esters by reaction with an appropriate alcohol and acid catalyst. Compounds with an ester group at the 5-pyridyl position can be reduced, for example, with sodium borohydride or lithium aluminum hydride to produce the corresponding 5-hydroxymethyl-substituted analogs. These analogs in turn can be converted to compounds bearing an alkoxymethyl moiety at the 5-pyridyl position by reaction, for example, with sodium hydride and an appropriate alkyl halide, using conventional techniques. Alternatively, the 5-hydroxymethyl-substituted analogs can be reacted with tosyl chloride to provide the corresponding 5-tosyloxymethyl analogs. The 5-carboxylic acid-substituted analogs can also be converted to the corresponding 5-alkylaminoacyl analogs by sequential treatment with thionyl chloride and an appropriate alkylamine. Certain of these amides are known to readily undergo nucleophilic acyl substitution to produce ketones. Thus, the so-called Weinreb amides (N-methoxy-N-methylamides) react with aryllithium reagents to produce the corresponding diaryl ketones. For example, see Selnick et al., *Tet. Lett.* 34: 2043 (1993).

5-Tosyloxymethyl-substituted analogs of the aforementioned compounds can be converted to the corresponding 5-methyl-substituted compounds by reduction with lithium aluminum hydride. 5-Tosyloxymethyl-substituted analogs of the aforementioned compounds can also be used to produce 5-alkyl-substituted compounds via reaction with an alkyl lithium salt. 5-Hydroxy-substituted analogs of the aforementioned compounds can be used to prepare 5-N-alkylcarbamoyloxy-substituted compounds by reaction with N-alkylisocyanates. 5-Amino-substituted analogs of the aforementioned compounds can be used to prepare 5-N-alkoxycarboxamido-substituted compounds by reaction with alkyl chloroformate esters, using techniques known to those skilled in the art of organic synthesis.

Analogous chemistries to the ones described hereinbefore for the preparation of the 5-substituted analogs of the azabicyclo analogs can be devised for the synthesis of 2-, 4-, and 6-substituted analogs, utilizing the appropriate 2-, 4-, or 6-aminopyrdyl intermediate, followed by diazotization to the corresponding diazonium salt, and then utilizing the same procedures for introducing the variety of substituents into the pyridine ring as was described for the 5-substituted analogs above. Similarly, by utilizing 2-, 4-, or 6-bromopyridyl derivatives of the above azabicyclo analogs, and subjecting each of these derivatives to the same procedures as described for introducing 5-substituents into the pyridyl ring from appropriate 5-bromo precursors of these azabicyclo analogs, additional 2-, 4-, or 6-substituents can be obtained in the manner described above.

Chiral auxiliary reagents that have been reported in the literature can be utilized in the synthesis of the pure enantiomers of 2-(3-pyridyl)-1-azabicyclo[2.2.1]heptane, 2-(3-pyridyl)-1-azabicyclo[2.2.2)octane, 2-(3-pyridyl)-1-azabicyclo[3.2.2]nonane, 7-(3-pyridyl)-1-azabicyclo[2.2.1]heptane, 7-(3-pyridyl)-1-azabicyclo[3.2.2]nonane, 3-(3-pyridyl)-1-azabicyclo[3.2.1]octane or 3-(3-pyridyl)-1-azabicyclo[3.2.2]nonane. See, as an example of this approach, reports by Enders and Reinhold, *Liebigs Ann.* (1): 11 (1996) and Enders and Whitehouse, *Synthesis* (5): 621 (1996). In these methods the chiral auxiliary agents, (S)-1-amino-2-(methoxymethyl)pyrrolidine (SAMP) and (S)-1-amino-2-(1-methoxy-1-methylethyl)pyrrolidine (SADP), or their respective R-isomers, are used to derivatize an appropriately substituted 3-pyridinecarboxaldehyde, to form the corresponding hydrazone. Treatment of the hydrazone with the required cyclic ether containing alkylmagnesium bromide, followed by deprotection with sodium/liquid ammonia will afford the appropriate enantiomerically pure precursor of the aforementioned azabicyclo compounds.

III. Pharmaceutical Compositions

The compounds described herein can be incorporated into pharmaceutical compositions and used to prevent a condition or disorder in a subject susceptible to such a condition or disorder, and/or to treat a subject suffering from the condition or disorder. The pharmaceutical compositions described herein include one or more compounds of Formula I and/or pharmaceutically acceptable salts thereof. Chiral compounds can be employed as racemic mixtures or as pure enantiomers.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions can be formulated in unit dose form, or in multiple or subunit doses. Preferred compositions are in liquid or semisolid form. Compositions including a liquid pharmaceutically inert carrier such as water or other pharmaceutically compatible liquids or semisolids can be used. The use of such liquids and semisolids is well known to those of skill in the art.

The compositions can also be administered via injection, i.e., intravenously, intramuscularly, subcutaneously, intraperitoneally, intraarterially, intrathecally; and intracerebroventricularly. Intravenous administration is the preferred method of injection. Suitable carriers for injection are well known to those of skill in the art and include 5% dextrose solutions, saline, and phosphate-buffered saline. The compounds can also be administered as an infusion or injection (e.g., as a suspension or as an emulsion in a pharmaceutically acceptable liquid or mixture of liquids).

The formulations can also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

Exemplary methods for administering such compounds will be apparent to the skilled artisan. The usefulness of these formulations can depend on the particular composition used and the particular subject receiving the treatment. These formulations can contain a liquid carrier that can be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, upon administration, the active ingredients interact with receptor sites within the body of the subject that affect the functioning of the CNS. More specifically, in treating a CNS disorder, preferable administration is designed to optimize the effect upon those relevant nicotinic acetylcholine receptor (nAChR) subtypes that have an effect upon the functioning of the CNS, while minimizing the effects upon muscle-type receptor subtypes. Other suitable methods for administering the compounds of the present invention are described in U.S. Pat. No. 5,604,231 to Smith et al., the contents of which are hereby incorporated by reference.

In certain circumstances, the compounds described herein can be employed as part of a pharmaceutical composition with other compounds intended to prevent or treat a particular disorder. In addition to effective amounts of the compounds described herein, the pharmaceutical compositions can also include various other components as additives or adjuncts. Exemplary pharmaceutically acceptable components or adjuncts which are employed in relevant circumstances include antioxidants, free-radical scavenging agents, peptides, growth factors, antibiotics, bacteriostatic agents, immunosuppressives, anticoagulants, buffering agents, anti-inflammatory agents, anti-pyretics, time-release binders, anesthetics, steroids, vitamins, minerals and corticosteroids. Such components can provide additional therapeutic benefit, act to affect the therapeutic action of the pharmaceutical composition, or act towards preventing any potential side effects that can be imposed as a result of administration of the pharmaceutical composition.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder.

When treating a CNS disorder, an effective amount of compound is an amount sufficient to pass across the blood-brain barrier of the subject, to bind to relevant receptor sites in the brain of the subject and to modulate the activity of relevant nAChR subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the recurrence of the symptoms of the disorder. Preferably, the effective amount is sufficient to obtain the desired result, but insufficient to cause appreciable side effects.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to modulate the activity of relevant nAChRs to effect neurotransmitter (e.g., dopamine) release, but the amount should be insufficient to induce effects on skeletal muscles and ganglia to any significant degree. The effective dose of compounds will of course differ from patient to patient, but in general includes amounts starting where CNS effects or other desired therapeutic effects occur but below the amount where muscular effects are observed.

The compounds, when employed in effective amounts in accordance with the method described herein, are selective to certain relevant nAChRs, but do not significantly activate receptors associated with undesirable side effects at concentrations at least greater than those required for eliciting the release of dopamine or other neurotransmitters. By this is meant that a particular dose of compound effective in preventing and/or treating a CNS disorder is essentially ineffective in eliciting activation of certain ganglionic-type nAChRs at concentration higher than 5 times, preferably higher than 100 times, and more preferably higher than 1,000 times than those required for modulation of neurotransmitter release. This selectivity of certain compounds described herein against those ganglionic-type receptors responsible for cardiovascular side effects is demonstrated by a lack of the ability of those compounds to activate nicotinic function of adrenal chromaffin tissue at concentrations greater than those required for activation of dopamine release.

The compounds described herein, when employed in effective amounts in accordance with the methods described herein, can provide some degree of prevention of the progression of CNS disorders, ameliorate symptoms of CNS disorders, and ameliorate to some degree of the recurrence of CNS disorders. The effective amounts of those compounds are typically below the threshold concentration required to elicit any appreciable side effects, for example those effects relating to skeletal muscle. The compounds can be administered in a therapeutic window in which certain CNS disorders are treated and certain side effects are avoided. Ideally, the effective dose of the compounds described herein is sufficient to provide the desired effects upon the CNS but is insufficient (i.e., is not at a high enough level) to provide undesirable side effects. Preferably, the compounds are administered at a dosage effective for treating the CNS disorders but less than ⅕, and often less than ⅒, the amount required to elicit certain side effects to any significant degree.

Most preferably, effective doses are at very low concentrations, where—maximal effects are observed to occur, with a minimum of side effects. Typically, the effective dose of such compounds generally requires administering the compound in an amount of less than 5 mg/kg of patient weight. Often, the compounds of the present invention are administered in an amount from less than about 1 mg/kg patent weight and usually less than about 100 μg/kg of patient weight, but frequently between about 10 μg to less than 100 μg/kg of patient weight. For compounds that do not induce effects on muscle-type nicotinic receptors at low concentrations, the effective dose is less than 5 mg/kg of patient weight; and often such compounds are administered in an amount from 50 μg to less than 5 mg/kg of patient weight. The foregoing effective doses typically represent that amount administered as a single dose, or as one or more doses administered over a 24-hour period.

For human patients, the effective dose of typical compounds generally requires administering the compound in an amount of at least about 1, often at least about 10, and frequently at least about 100 mg/24 hr/patient. For human patients, the effective dose of typical compounds requires administering the compound which generally does not exceed about 500, often does not exceed about 400, and frequently does not exceed about 300 mg/24 hr/patient. In addition, the compositions are advantageously administered at an effective dose such that the concentration of the compound within the plasma of the patient normally does not exceed 50 ng/mL, often does not exceed 30 ng/mL, and frequently does not exceed 10 ng/ml.

IV. Methods of Using the Compounds and/or Pharmaceutical Compositions

The compounds can be used to treat those types of conditions and disorders for which other types of nicotinic compounds have been proposed as therapeutics. See, for example, Williams et al., *Drug News Perspec.* 7(4):205 (1994), Arneric et al., *CNS Drug Rev.* 1(1): 1 (1995), Arneric et al., *Exp. Opin. Invest. Drugs* 5(1):79 (1996), Bencherif et al., *J. Pharmacol. Exp. Ther.* 279:1413 (1996), Lippiello et al., *J. Pharmacol. Exp. Ther.* 279:1422 (1996), Damaj et al., *J. Pharmacol. Exp. Ther.* 291:390 (1999); Chiari et al., *Anesthesiology* 91:1447 (1999); Lavand'homme and Eisenbach, *Anesthesiology* 91:1455 (1999); *Neuroscience* (1997), Holladay et al., *J. Med. Chem.* 40(28):4169 (1997), Bannon et al., *Science* 279:77 (1998), PCT WO 94/08992, PCT WO 96/31475, and U.S. Pat. No. 5,583,140 to Bencherif et al., U.S. Pat. No. 5,597,919 to Dull et al., and U.S. Pat. No. 5,604,231 to Smith et al., the disclosures of each of which are incorporated herein by reference in their entirety.

More particularly, the compounds can be used to treat those types of conditions and disorders for which nicotinic compounds with selectivity for the α7 nAChR subtype have been proposed as therapeutics. See, for example, Leonard et al., *Schizophrenia Bulletin* 22(3): 431 (1996), Freedman et al., *Biol. Psychiatry* 38(1): 22 (1995), Heeschen et al., *J. Clin. Invest.* 100: 527 (2002), Utsugisawa et al., *Molecular Brain Research* 106(1–2): 88 (2002), U.S. Patent Application 2002/0016371, Levin and Rezvani, *Current Drug Targets: CNS and Neurological Disorders* 1(4): 423 (2002)), O'Neill et al., *Current Drug Targets: CNS and Neurological Disorders* 1(4): 399 (2002, Jeyarasasingam et al., *Neuroscience* 109(2): 275 (2002)), Xiao et al., *Proc. Nat. Acad. Sci.* (US) 99(12): 8360 (2002)), PCT WO 99/62505, PCT WO 99103859, PCT WO 97/30998, PCT WO 01/36417, PCT WO 02/15662, PCT WO 02/16355, PCT WO 02/16356, PCT WO 02/16357, PCT WO 02/16358, PCT WO 02/17358, Stevens et al., *Psychopharm.* 136: 320 (1998), Dolle et al., *J. Labelled Comp. Radiopharm.* 44: 785 (2001) and Macor et al., *Bioorg. Med. Chem. Lett.* 11: 319 (2001) and references therein, the contents of each of which are hereby incorporated by reference in their entirety.

The compounds can also be used as adjunct therapy in combination with existing therapies in the management of the aforementioned types of diseases and disorders. In such situations, it is preferably to administer the active ingredients in a manner that minimizes effects upon nAChR subtypes such as those that are associated with muscle and ganglia. This can be accomplished by targeted drug delivery and/or by adjusting the dosage such that a desired effect is obtained without meeting the threshold dosage required to achieve significant side effects. The pharmaceutical compositions can be used to ameliorate any of the symptoms associated with those conditions, diseases and disorders. Representative classes of disorders that can be treated are discussed in detail below.

Treatment of CNS Disorders

Examples of conditions and disorders that can be treated include neurological disorders and neurodegenerative disorders, and, in particular, CNS disorders. CNS disorders can be drug induced; can be attributed to genetic predisposition, infection or trauma; or can be of unknown etiology. CNS disorders comprise neuropsychiatric disorders, neurological diseases and mental illnesses, and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of choline, dopamine, norepinephrine and/or serotonin.

Examples of CNS disorders that can be treated in accordance with the present invention include pre-senile dementia (early onset Alzheimer's disease), senile dementia (dementia of the Alzheimer's type), Lewy Body dementia, microinfarct dementia, AIDS-related dementia, HIV-dementia, multiple cerebral infarcts, Parkinsonism including Parkinson's disease, Pick's disease, progressive supranuclear palsy, Huntington's chorea, tardive dyskinesia, hyperkinesia, mania, attention deficit disorder, anxiety, depression, dyslexia, schizophrenia depression, obsessive-compulsive disorders, Tourette's syndrome, mild cognitive impairment (MCI), age-associated memory impairment (AAMI), premature amnesic and cognitive disorders which are age-related or a consequence of alcoholism, or immunodeficiency syndrome, or are associated with vascular disorders, with genetic alterations (such as, for example, trisomy 21) or with attention deficiencies or learning deficiencies, acute or chronic neurodegenerative conditions such as amyotrophic lateral sclerosis, multiple sclerosis, peripheral neurotrophies, and cerebral or spinal traumas. In addition, the compounds can be used to treat nicotine addiction and/or other behavioral disorders related to substances that lead to dependency (e.g., alcohol, cocaine, heroin and opiates, psychostimulants, benzodiazepines and barbiturates).

Schizophrenia is an example of a CNS disorder that is particularly amenable to treatment by modulating the α7 nAChR subtype. The compounds can also be administered to improve cognition and/or provide neuroprotection, and these uses are also particularly amenable to treatment with compounds, such as the compounds of the present invention, that are specific for the α7 nAChR subtype.

The disorders can be treated and/or prevented by administering to a patient in need of treatment or prevention thereof an effective treatment or preventative amount of a compound that provides some degree of prevention of the progression of a CNS disorder (i.e., provides protective effects), ameliorating the symptoms of the disorder, and ameliorating the recurrence of the disorder.

Anti-inflammatory Uses

Excessive inflammation and tumor necrosis factor synthesis cause morbidity and even mortality in a variety of diseases. These diseases include, but are not limited to, endotoxemia, sepsis, rheumatoid arthritis, and irritable bowel disease. The nervous system, primarily through the vagus nerve, is known to regulate the magnitude of the innate immune response by inhibiting the release of macrophage tumor necrosis factor (TNF). This physiological mechanism is known as the "cholinergic anti-inflammatory pathway" (see, for example, Tracey, *Nature* 420: 853 (2002)).

The nicotinic acetylcholine receptor (α7 subunit is required for acetylcholine inhibition of macrophage TNF release, and also inhibits release of other cytokines. Agonists (or, at elevated dosages, partial agonists) at the α7-specific receptor subtype can inhibit the TNF-modulated inflammatory response. Accordingly, those compounds described herein that are α7 agonists can be used to treat inflammatory disorders characterized by excessive synthesis of TNF (see also Wang et al., *Nature* 421: 384 (2003)).

Inflammatory conditions that can be treated or prevented by administering the compounds described herein include, but are not limited to, chronic and acute inflammation, psoriasis, gout, acute pseudogout, acute gouty arthritis, arthritis, rheumatoid arthritis, osteoarthritis, allograft rejection, chronic transplant rejection, asthma, atherosclerosis, mononuclear-phagocyte dependent lung injury, idiopathic pulmonary fibrosis, atopic dermatitis, chronic obstructive pulmonary disease, adult respiratory distress syndrome, acute chest syndrome in sickle cell disease, inflammatory bowel disease, Crohn's disease, ulcerative colitis, acute cholangitis, aphteous stomatitis, glomerulonephritis, lupus nephritis, thrombosis, and graft vs. host reaction. Fibromyalgia syndrome can also be treated with agonists of the α7 receptor.

Minimizing the Inflammatory Response Associated with Bacterial and/or Viral Infection Many bacterial and/or viral infections are associated with side effects brought on by the formation of toxins, and the body's natural response to the bacteria or virus and/or the toxins. Examples of such bacterial infections include anthrax, botulism, and sepsis. As discussed above, the body's response to infection often involves generating a significant amount of TNF and/or other cytokines. The over-expression of these cytokines can result in significant injury, such as septic shock (when the bacteria is sepsis), endotoxic shock, urosepsis and toxic shock syndrome.

Cytokine expression is mediated by the α7 nAChR, and can be inhibited by administering agonists or partial agonists of these receptors. Those compounds described herein that are agonists or partial agonists of these receptors can therefore be used to minimize the inflammatory response associated with bacterial infection, as well as viral and fungal infections. Certain of the compounds themselves may also have antimicrobial properties.

These compounds can also be used as adjunct therapy in combination with existing therapies to manage bacterial, viral and fungal infections, such as antibiotics, antivirals and antifungals. Antitoxins can also be used to bind to toxins produced by the infectious agents and allow the bound toxins to pass through the body without generating an inflammatory response. Examples of antitoxins are disclosed, for example, in U.S. Pat. No. 6,310,043 to Bundle et al., incorporated herein by reference. Other agents effective against bacterial and other toxins can be effective and their therapeutic effect can be complimented by co-administration with the compounds described herein.

Analgesic Uses

The compounds can be administered to treat and/or prevent pain, including neurologic, neuropathic and chronic pain. The analgesic activity of compounds described herein can be demonstrated in models of persistent inflammatory pain and of neuropathic pain, performed as described in U.S. Published Patent Application No. 20010056084 A1 to Allgeier et al. (e.g., mechanical hyperalgesia in the complete Freund's adjuvant rat model of inflammatory pain and mechanical hyperalgesia in the mouse partial sciatic nerve ligation model of neuropathic pain).

The analgesic effect is suitable for treating pain of various genesis or etiology, in particular in treating inflammatory pain and associated hyperalgesia, neuropathic pain and associated hyperalgesia, chronic pain (e.g., severe chronic pain, post-operative pain and pain associated with various conditions including cancer, angina, renal or billiary colic, menstruation, migraine and gout). Inflammatory pain may be of diverse genesis, including arthritis and rheumatoid disease, teno-synovitis and vasculitis. Neuropathic pain includes trigeminal or herpetic neuralgia, diabetic neuropathy pain, causalgia, low back pain and deafferentation syndromes such as brachial plexus avulsion.

Inhibition of Neovascularization

The α7 nAChR is also associated with neovascularization. Inhibition of neovascularization, for example, by administering antagonists (or at certain dosages, partial agonists) of the α7 nAChR can treat or prevent conditions characterized by undesirable neovascularization or angiogenesis. Such conditions can include those characterized by inflammatory angiogenesis and/or ischemia-induced angiogenesis. Neovascularization associated with tumor growth can also be inhibited by administering those compounds described herein that function as antagonists or partial agonists of α7 nAChR.

Specific antagonism of α7 nAChR-specific activity reduces the angiogenic response to inflammation, ischemia, and neoplasia. Guidance regarding appropriate animal model systems for evaluating the compounds described herein can be found, for example, in Heeschen et al., *J. Clin. Invest.* 110(4): 527 (2002), incorporated herein by reference regarding disclosure of α7-specific inhibition of angiogenesis and cellular (in vitro) and animal modeling of angiogenic activity relevant to human disease, especially the Lewis lung tumor model (in vivo, in mice—see, in particular, pages 529, and 532–533).

Representative tumor types that can be treated using the compounds described herein include NSCLC, ovarian cancer, pancreatic cancer, breast carcinoma, colon carcinoma, rectum carcinoma, lung carcinoma, oropharynx carcinoma, hypopharynx carcinoma, esophagus carcinoma, stomach carcinoma, pancreas carcinoma, liver carcinoma, gallbladder carcinoma, bile duct carcinoma, small intestine carcinoma, urinary tract carcinoma, kidney carcinoma, bladder carcinoma, urothelium carcinoma, female genital tract carcinoma, cervix carcinoma, uterus carcinoma, ovarian carcinoma, choriocarcinoma, gestational trophoblastic disease, male genital tract carcinoma, prostate carcinoma, seminal vesicles carcinoma, testes carcinoma, germ cell tumors, endocrine gland carcinoma, thyroid carcinoma, adrenal carcinoma, pituitary gland carcinoma, skin carcinoma, hemangiomas, melanomas, sarcomas, bone and soft tissue sarcoma, Kaposi's sarcoma, tumors of the brain, tumors of the nerves, tumors of the eyes, tumors of the meninges, astrocytomas, gliomas, glioblastomas, retinoblastomas, neuromas, neuroblastomas, Schwannomas, meningiomas, solid tumors arising from hematopoietic malignancies (such as leukemias, chloromas, plasmacytomas and the plaques and tumors of mycosis fingoides and cutaneous T-cell lymphoma/leukemia), and solid tumors arising from lymphomas.

The compounds can also be administered in conjunction with other forms of anti-cancer treatment, including co-administration with antineoplastic antitumor agents such as cis-platin, adriamycin, daunomycin, and the like, and/or anti-VEGF (vascular endothelial growth factor) agents, as such are known in the art.

The compounds can be administered in such a manner that they are targeted to the tumor site. For example, the compounds can be administered in microspheres, microparticles or liposomes conjugated to various antibodies that direct the microparticles to the tumor. Additionally, the compounds can be present in microspheres, microparticles or liposomes that are appropriately sized to pass through the arteries and veins, but lodge in capillary beds surrounding tumors and administer the compounds locally to the tumor. Such drug delivery devices are known in the art.

Other Disorders

In addition to treating CNS disorders, inflammatory disorders, and neovascular disorders, and inhibiting the pain response, the compounds can be also used to prevent or treat certain other conditions, diseases, and disorders. Examples include autoimmune disorders such as Lupus, disorders associated with cytokine release, cachexia secondary to infection, e.g., as occurs in AIDS, AIDS related complex and neoplasia), as well as those indications set forth in PCT WO 98/25619. The compounds can also be administered to treat convulsions such as those that are symptomatic of epilepsy, and to treat conditions such as syphillis and Creutzfeld-Jakob disease.

Diagnostic Uses

The compounds can be used in diagnostic compositions, such as probes, particularly when they are modified to include appropriate labels. The probes can be used, for example, to determine the relative number and/or function of specific receptors, particularly the α7 receptor subtype. The compounds of the present invention most preferably are labeled with a radioactive isotopic moiety such as $^{11}C$, $^{18}F$, $^{76}Br$, $^{123}I$ or $^{125}I$, as discussed in PCT WO01/82979 to Bencherif et al.

The administered compounds can be detected using known detection methods appropriate for the label used. Examples of detection methods include position emission topography (PET) and single-photon emission computed tomography (SPECT). The radiolabels described above are useful in PET (e.g., $^{11}C$, $^{18}F$ or $^{76}Br$) and SPECT (e.g., $^{123}I$) imaging, with half-lives of about 20.4 minutes for $^{11}C$, about 109 minutes for $^{18}F$, about 13 hours for $^{123}I$, and about 16 hours for $^{76}Br$. A high specific activity is desired to visualize the selected receptor subtypes at non-saturating concentrations. The administered doses typically are below the toxic range and provide high contrast images. The compounds are expected to be capable of administration in non-toxic levels. Determination of dose is carried out in a manner known to one skilled in the art of radiolabel imaging. See, for example, U.S. Pat. No. 5,969,144 to London et al.

The compounds can be administered using known techniques. See, for example, U.S. Pat. No. 5,969,144 to London et al. The compounds can be administered in formulation compositions that incorporate other ingredients, such as those types of ingredients that are useful in formulating a diagnostic composition. Compounds useful in accordance with carrying out the present invention most preferably are employed in forms of high purity. See U.S. Pat. No. 5,853,696 to Elmalch et al.

After the compounds are administered to a subject (e.g., a human subject), the presence of that compound within the subject can be imaged and quantified by appropriate techniques in order to indicate the presence, quantity, and functionality of selected nicotinic cholinergic receptor subtypes. In addition to humans, the compounds can also be administered to animals, such as mice, rats, dogs, and monkeys. SPECT and PET imaging can be carried out using any appropriate technique and apparatus. See Villemagne et al., In: *Neuronal Nicotinic Receptors: Pharmacology and Therapeutic Opportunities*, Arneric et al. (Eds.), 235–250 (1998) and U.S. Pat. No. 5,853,696 to Elmalch et al. for a disclosure of representative imaging techniques.

The radiolabeled compounds bind with high affinity to selective nAChR subtypes (e.g., α7) and preferably exhibit negligible non-specific binding to other nicotinic cholinergic receptor subtypes (e.g., those receptor subtypes associated with muscle and ganglia). As such, the compounds can be used as agents for noninvasive imaging of nicotinic cholinergic receptor subtypes within the body of a subject, particularly within the brain for diagnosis associated with a variety of CNS diseases and disorders.

In one aspect, the diagnostic compositions can be used in a method to diagnose disease in a subject, such as a human patient. The method involves administering to that patient a detectably labeled compound as described herein, and detecting the binding of that compound to selected nicotinic receptor subtypes (e.g., α7 receptor subtype). Those skilled in the art of using diagnostic tools, such as PET and SPECT, can use the radiolabeled compounds described herein to diagnose a wide variety of conditions and disorders, including conditions and disorders associated with dysfunction of the central and autonomic nervous systems. Such disorders include a wide variety of CNS diseases and disorders, including Alzheimer's disease, Parkinson's disease, and schizophrenia. These and other representative diseases and disorders that can be evaluated include those that are set forth in U.S. Pat. No. 5,952,339 to Bencherif et al., the contents of which are hereby incorporated by reference.

In another aspect, the diagnostic compositions can be used in a method to monitor selective nicotinic receptor subtypes of a subject, such as a human patient. The method involves administering a detectably labeled compound as described herein to that patient and detecting the binding of that compound to selected nicotinic receptor subtypes (e.g., the α7 receptor subtype).

The following examples are provided to further illustrate the present invention, and should not be construed as limiting thereof.

V. SYNTHETIC EXAMPLES

The following examples are provided to further illustrate the present invention, and should not be construed as limiting thereof.

Example 1

Sample No. 1 is (+/−)-2-(3-pyridyl)-1-azabicyclo[2.2.2] octane, which is prepared in accordance with the techniques set forth in U.S. Pat. No. 5,559,124, the disclosure of which is incorporated herein by reference in its entirety.

Example 2

Sample No. 2 is (+/−)-2-(5-bromo-3-pyridyl)-1-azabicyclo[2.2.2]octane, which is prepared in accordance with the following techniques. The techniques employed in the synthesis of the oxanyl-4-methanol are described by Thomas and Clough, *J. Pharm. Pharmacology*, 15: 167 (1963).

Diethyl oxane-4,4-dicarboxylate

Sodium (20.7 g, 900 mmol) was carefully dissolved in dry ethanol (300 mL) and to this mixture was added diethyl malonate (144 g, 900 mmol) and 2, bis-(2-chloroethyl)ether (129 g, 900 mmol). The reaction mixture was refluxed for 15 h and cooled to room temperature. The solvent was removed by rotary evaporation, the product acidified with 10% HCl (200 mL), extracted with ethyl acetate (4×200 mL) and dried ($Na_2SO_4$). Removal of solvent by rotary evaporation, followed by distillation (170–175° C., 22 mm Hg) furnished the product (98.0 g, 48% yield).

Oxane-4,4-dicarboxylic Acid

To a stirred solution of diethyl oxane-4,4-dicarboxylate (40.0 g., 173 mmol) in ethanol (100 mL) was added a solution of potassium hydroxide (21.4 g, 382 mmol) in ethanol (300 mL). After the completion of the addition, the reaction mixture was stirred for 15 min at ambient temperature and then refluxed for 2.5 h. Water (40 mL) was added to the thick, white suspension, and then the solvent was removed by rotary evaporation. Water (40 mL) was added to the remaining residue and the resulting mixture then acidified with concentrated sulfuric acid (20 mL). The acidic solution was extracted with diethyl ether (3×300 mL) and the combined organic layers were dried ($Na_2SO_4$). Removal of solvent by rotary evaporation yielded the product (27.3 g, 90.2% yield).

Oxane-4-carboxylic Acid

Oxane-4,4-dicarboxylic acid was taken in a round bottom flask fitted with a reflux condenser and was gradually heated to 180° C. When evolution of carbon dioxide decreased, the reaction was allowed to cool to room temperature. The monoacid thus obtained was purified by distillation (160–165° C. at 22 mm Hg) to yield oxane-4-carboxylic acid (16.1 g, 71.8% yield).

Oxanyl-4-methanol

To a stirred solution of lithium aluminum hydride (13.99 g, 368 mmol) in dry tetrahydrofuran (THF, 50 mL) was added dry THF (50 mL) and oxane-4-carboxylic acid (15.96 g, 123 mmol). The reaction mixture was refluxed for 24 h, then cooled to 0° C. and a solution of sodium hydroxide (30%, 25 mL) was added drop-wise. The solid thus obtained was filtered off and repeatedly washed with THF. The filtrate was dried over anhydrous sodium carbonate. Removal of solvent, followed by purification by column chromatography, furnished the alcohol, oxanyl-4-methanol (13.1 g, 91.6% yield).

(4-Oxanyl)methyl methanesulfonate

To a stirring solution of oxanyl-4-methanol (10.0 g, 89 mmol) in dry dichloromethane (50 mL) and triethylamine (16.1 mL, 11.7 g, 16.1 mmol) was added methanesulfonyl chloride (8.98 ml., 13.3 g, 16.1 mmol) drop-wise at 0° C. under a $N_2$ atmosphere. The reaction mixture was stirred overnight, during which time it came to ambient temperature. The reaction mixture was washed with saturated aqueous $Na_2CO_3$ (25 mL) and the aqueous layer was extracted with dichloromethane (50 mL). The combined organic extracts were dried ($K_2CO_3$), filtered and concentrated by rotary evaporation. This afforded a brown viscous liquid, which solidified upon standing at ambient temperature. The solid was triturated with hexane and the triturates discarded. Drying of the residue gave 15.0 g of light brown solid (84% yield).

3-Bromo-5-hydroxymethylpyridine

3-Bromo-5-hydroxymethylpyridine can be prepared according to one of two techniques.

Method A: Ethyl 5-bromo-3-nicotinate is prepared by dissolving 5-bromo-3-nicotinic acid (50.00 g, 247.5 mmol)

in ethyl alcohol (130 mL) at room temperature. To this solution was added drop-wise concentrated sulfuric acid (50.0 mL, 938 mmol) with constant stirring. After completion of the addition, the reaction mixture was refluxed for 40 h and then cooled to 0° C., followed by neutralization with saturated sodium carbonate solution (pH=8). The neutralized solution was extracted with chloroform (3×200 mL) and dried ($Na_2SO_4$). Removal of solvent by rotary evaporation furnished ethyl 5-bromo-3-nicotinate (39.85 g, 97% yield).

Ethyl 5-bromo-3-nicotinate is reduced by adding sodium borohydride (29.6 g., 782.6 mmol) to a stirred solution of ethyl 5-bromo-3-nicotinate (20 g, 86.9 mmol) in ethyl alcohol (450 mL). The reaction mixture was refluxed for 30 h and then the solvent was removed by rotary evaporation. The solid thus obtained was treated with 10% dilute hydrochloric acid (3N, 40 mL) to pH 6, and the resulting aqueous solution extracted with ethyl acetate (3×200 mL) and dried ($Na_2SO_4$). Removal of solvent by rotary evaporation, followed by purification by column chromatography, furnished 3-bromo-5-hydroxymethyl pyridine (8.5 g, 52% yield).

Method B: To a suspension of 5-bromonicotinic acid (1.0 g, 4.9 mmol) in benzene (20 mL) was added triethylamine (0.73 mL, 5.2 mmol) at room temperature. After stirring for 5 min, ethyl chloroformate (0.50 mL, 5.2 mmol) was added and the mixture was stirred for a further 1 h at room temperature. The triethylamine hydrochloride salt thus precipitated was filtered off and the filtrate was evaporated to dryness to give the mixed anhydride, which was not further purified. It was taken up in dry THF (26 mL) and the solution immediately added to a stirred suspension of lithium aluminum hydride (0.2 g, 5.29 mmol) in dry THF (7 mL) at −78° C. This mixture was stirred for 30 min at −78° C. Workup in the usual manner, followed by purification by column chromatography, yielded 3-bromo-5-hydroxymethylpyridine (0.762 g, 82% yield).

(5-Bromo-3-pyridyl)methylamine (5-Bromo-3-pyridyl)methylamine can be prepared according to one of two techniques.

Method A: 5-Bromo-3-(phthalimidomethyl)pyridine is produced by adding triphenylphosphine (12.1 g, 46.3 mmol) and phthalimide (6.80 g, 46.3 mmol) in dry THF (70 mL) to a stirred suspension of 3-bromo-5-hydroxymethylpyridine (6.70 g, 35.6 mmol), and then adding a solution of diethyl azodicarboxylate (7.30 mL, 46.3 mmol) in dry THF (30 mL) drop-wise. The reaction mixture was stirred at room temperature overnight. After removal of the solvent by rotary evaporation, the crude material was purified by column chromatography to yield 5-bromo-3-(phthalimidomethyl) pyridine (9.5 g, 85% yield).

5-Bromo-3-(phthalimidomethyl)pyridine (7.9 g, 25 mmol) is then hydrolyzed by treatment with aqueous methylamine (40%, 50 mL) and refluxing the mixture for 3 h. The solvents were removed by rotary evaporation to yield a pale yellow-colored solid, which was then taken up into concentrated hydrochloric acid (50 mL) and refluxed for 15 h. The reaction mixture was basified (pH=10–11) with aqueous sodium hydroxide (50%), extracted with chloroform (5×40 mL) and dried ($K_2CO_3$). The solvent was removed by rotary evaporation and the product purified by column chromatography to yield (5-bromo-3-pyridyl)methylamine (2.80 g, 59.8% yield).

Method B: 3-Bromo-5-hydroxymethylpyridine (1.1 g, 5.8 mmol) was added to thionyl chloride (5 mL) at 0° C. under nitrogen over 5 min. The solution was stirred at room temperature for 1 h, re-cooled to 0° C., and dry ether (40 mL) was added. The resulting solid was filtered off, washed with ether and added to a stirred solution of ammonia (28%, 30 mL) and ethyl alcohol (40 mL) at 0° C. The solution was then stirred at room temperature for 20 h. The solvent was removed by rotary evaporation and the crude material partitioned between sodium hydroxide (2N, 30 mL) and dichloromethane (60 mL). The organic layer was dried ($Na_2SO_4$), the solvent removed by rotary evaporation and the residue purified by flash chromatography, using $CHCl_3$: ethanol: concentrated aqueous ammonia solution (100:6:1) as eluent, to afford (5-bromo-3-pyridyl)methylamine (785 mg, 72% yield).

5-Bromo-N-(diphenylmethylidene)-3-(aminomethyl)pyridine

To a solution of (5-bromo-3-pyridyl)methylamine (1.50 g, 8.02 mmol) in dry toluene (5 mL) was added benzophenone (1.60 g, 8.79 mmol) and p-toluenesulfonic acid (PTSA, 2 mg). The reaction mixture was refluxed for 48 h using a Dean-Stark apparatus. After completion of the reaction, the solvent was removed in vacuum and the crude material was purified by column chromatography to yield 5-bromo-N-(diphenylmethylidene)-3-(aminomethyl)-pyridine (1.9 g, 56% yield).

2-(4-Oxanyl)-1-(5-bromo-3-pyridyl)ethylamine

To a solution of diisopropylamine (0.550 mL, 3.92 mmol) in dry THF (3 mL) was added n-butyllithium (2.45 mL, 1.6 M solution in THF) at 0° C. This mixture was then added via cannula to a stirred suspension of 5-bromo-N-(diphenylmethylidene)-3-(aminomethyl)pyridine (1.00 g, 3.01 mmol) in dry THF (10 mL) at −78° C., and the reaction mixture was stirred for 45 min at −78° C. 4-Oxanylmethyl methanesulfonate (0.706 g, 3.92 mmol) in dry THF at −78° C. was then added. The reaction mixture was allowed to warm to ambient temperature, followed by additional stirring for 12 h. The reaction mixture was quenched with hydrochloric acid (10% w/v, 20 mL) and stirred for 30 min, followed by extraction with ethyl acetate (3×25 mL). The resulting aqueous solution was made basic (pH=8–9) by adding solid potassium carbonate and the mixture extracted with chloroform (3×25 mL). The combined organic layers were dried over anhydrous potassium carbonate. Removal of solvent by rotary evaporation and purification of the residue by column chromatography furnished 2-(4-oxanyl)-1-(5-bromo-3-pyridyl)ethylamine as a pale-yellow colored syrup, which could not be distilled (600 mg, 70% yield).

(+/−)-2-(5-Bromo-3-pyridyl)-1-azabicyclo[2.2.2]octane dihydrochloride 2-(4-Oxanyl)-1-(5-bromo-3-pyridyl)ethylamine (500 mg, 1.76 mmol) was dissolved in aqueous hydrobromic acid (48%, 10 mL) and hydrogen bromide gas was passed through the solution until saturated. The reaction mixture was then carefully transferred to a pressure tube and heated at 120° C. for 16 h. The reaction mixture was allowed to cool to ambient temperature and then transferred to a round bottom flask. HBr was removed by rotary evaporation. The resulting dark brown residue was taken up into absolute ethanol and the solution heated with potassium carbonate (3 g) for 12 h. The reaction mixture was cooled to room temperature and filtered through a Celite pad. Removal of solvent by rotary evaporation, followed by purification of the resulting residue by column chromatography, yielded the desired product (150 mg, 32% yield).

2-(5-Bromo-3-pyridyl)-1-azabicyclo[2.2.2]octane free base (90 mg, 0.33 mmol) was dissolved in ethanolic HCl (5 mL) and the mixture sonicated for 5 min. The solvent was removed by rotary evaporation to yield a solid residue, which was recrystallized from isopropanol, to afford the dihydrochloride salt as a light brown crystalline solid (100 mg).

Example 3

Sample No. 3 is exo 2-(3-pyridyl)-1-azabicyclo[2.2.1] heptane, which is prepared according to the following techniques.

N-(Diphenylmethylidene)-3-(aminomethyl)pyridine

Benzophenone (10.92 g, 60 mmol), 3-(aminomethyl)pyridine (6.48 g, 60 mmol) and p-toluenesulfonic acid (10 mg) were dissolved in 30 ml benzene and the reaction mixture was heated to reflux under a nitrogen atmosphere using a Dean-Stark apparatus. The completion of the reaction (12–16 h) was determined when the calculated amount of water was collected in the Dean-Stark apparatus. Benzene was removed by rotary evaporation and the resulting N-(diphenylmethylidene)-3-(aminomethyl)pyridine was used in the next step without further purification.

3-Oxolanylmethyl Methanesulfonate

Methanesulfonyl chloride (18 mmol, 1.39 mL) was added to a flask containing oxolanyl-3-methanol (1.53 g, 15.0 mmol) in THF (25 mL) and triethylamine (3.13 mL, 22.5 mmol) at 0° C. under a nitrogen atmosphere. The cooling bath was removed and the reaction mixture was stirred overnight. A saturated solution of NaHCO$_3$ (15 mL) was added to the reaction mixture, followed by extraction with diethyl ether (3×15 mL). The combined organic extracts were dried over anhydrous magnesium sulfate. Filtration of the drying agent followed by concentration by rotary evaporation yielded the product as a pale yellow solid (2.13 g), which was used in the next step without further purification.

2-(3-Oxolanyl)-1-(3-pyridyl)ethylamine

Lithium diisopropylamide (LDA, 15 mmol) was generated at 0° C. by adding n-butyllithiumBuLi (6.4 mL, 2.3 M solution in hexane, 15 mmol) to a solution of diisopropylamine (2.27 mL, 16.0 mmol) in dry THF (13 mL). N-(diphenylmethylidene)-3-(aminomethyl)pyridine (3.62 g, 13.3 mmol) was dissolved in dry THF (13 mL) and the solution cooled to –78° C. under a nitrogen atmosphere. The LDA was then transferred via cannula to the solution of N-(diphenylmethylidene)-3-(aminomethyl)pyridine under a positive nitrogen atmosphere. The resulting purple suspension was stirred for a further 45 min, during which time the temperature of the reaction mixture was allowed to rise to –4° C. 3-Oxolanylmethyl methanesulfonate (2.64 g, 14.7 mmol) in THF (10 mL) was then added via syringe, and the reaction mixture was allowed to warm to ambient temperature, followed by additional stirring for 12 h. Hydrochloric acid (10% aq., 20 mL) was added and the reaction mixture was stirred for 20–30 min, followed by extraction with ethyl acetate (3×25 mL). The resulting aqueous solution was first made basic by adding solid K$_2$CO$_3$, then extracted with chloroform (3×25 mL). The combined chloroform extracts were dried (K$_2$CO$_3$) and filtered, followed by rotary evaporation of chloroform to yield 2-(3-oxolanyl)-1-(3-pyridyl) ethylamine as a diastereomeric (50:50) mixture (pale yellow oil, 2.03 g), which was used in the next step without further purification.

Exo-2-(3-pyridyl)-1-azabicyclo[2.2.1]heptane 2-(3-Oxolanyl)-1-(3-pyridyl)ethylamine (960 mg, 5.0 mmol) was dissolved in hydrobromic acid (48% aq., 12 mL).

Hydrogen bromide gas was generated according to the procedure described in *Vogel's Textbook of Practical Organic Chemistry*, 5th ed., Longman Scientific & Technical, 1991, pp 437–438, in which bromine is added drop-wise to tetralin, and the HBr gas thus generated was passed through the acidic solution of 2-(3-oxolanyl)-1-(3-pyridyl) ethylamine until saturated. The solution was then carefully transferred to a pressure tube and heated at 100° C. under pressure for 16 h. The tube was allowed to cool to ambient temperature and the contents then transferred to a round bottom flask. The mixture was basified with solid K$_2$CO$_3$ followed by stirring for 2 h. The reaction mixture was then extracted with chloroform (3×15 mL). The combined organic extracts were dried (K$_2$CO$_3$), filtered and concentrated by rotary evaporation to yield 700 mg of product as a dark brown oil. Separation of the endo and exo isomers in the product was achieved by column chromatography using methanol:chloroform (15:85, v/v) as the eluent. The fractions with $R_f$ value 0.43 (on TLC plates using the same solvent system) were concentrated by rotary evaporation to obtain crude exo-2-(3-pyridyl)-1-azabicyclo[2.2.1]heptane as a pale brown oil (190 mg), which was distilled under vacuum (92–95° C., 0.0025 mm Hg) to obtain 115 mg (13.2%) of pure product as a colorless oil.

Example 4

Sample No. 4 is endo-2-(3-pyridyl)-1-azabicyclo[2.2.1] heptane, which was isolated in accordance with the following techniques.

The fractions from Example 3 containing the endo isomer with an $R_f$ value of 0.33 (on TLC plates using methanol: chloroform (15:85, v/v) as the eluting solvent) were concentrated by rotary evaporation to afford crude endo-2-(3-pyridyl)-1-azabicyclo[2.2.1]heptane as a pale brown oil, which was distilled (101–104° C., 0.0025 mm Hg) to obtain 80 mg (9.1%) of pure endo-2-(3-pyridyl)-1-azabicyclo [2.2.1]heptane as a colorless oil.

Example 5

Sample No. 5 is 7-(3-pyridyl)-1-azabicyclo[2.2.1]heptane, which was prepared according to the following techniques.

1-(4-Oxanyl)-1-(3-pyridyl)methylamine

The 1-(4-oxanyl)-1-(3-pyridyl)methylamine was synthesized essentially according to the procedure described above for the synthesis of 1-(3-oxolanyl)-2-(3-pyridyl)ethylamine. Thus, 4-oxanyl methanesulfonate (0.99 g, 5.5 mmol), prepared according to the procedure of Suto et al., *J. Med. Chem.*, 34: 2484 (1991), was treated with the imine anion generated by reacting N-(diphenylmethylidene)-3-(aminomethyl)pyridine (1.36 g, 5.0 mmol) with LDA (5.5 mmol in 5.0 mL THF). A work up similar to the one described for the synthesis of 1-(3-oxolanyl)-2-(3-pyridyl)ethylamine, followed by purification by column chromatography (15% methanol in chloroform), yielded 1-(4-oxanyl)-1-(3-pyridyl) methylamine (499 mg, 52% yield).

7-(3-Pyridyl)-1-azabicyclo[2.2.1]heptane Treatment of 1-(4-oxanyl)-1-(3-pyridyl)methylamine (576 mg, 3.0 mmol) with hydrobromic acid, as described for the synthesis of the 2-(3-pyridyl)-1-azabicyclo[2.2.1]heptanes, resulted in formation of the crude desired product as a dark brown oil. It was purified by column chromatography (15% methanol in chloroform), followed by distillation (90° C., 0.005 mm Hg) under reduced pressure, to obtain the product as a colorless oil (260 mg, 51% yield).

Example 6

Sample No. 6 is 2-(5-amino-3-pyridyl)-1-azabicyclo[2.2.2]octane trihydrochloride, which was prepared in accordance with the following techniques.

2-(5-Amino-3-pyridyl)-1-azabicyclo[2.2.2]octane trihydrochloride 2-(5-Bromo-3-pyridyl)-1-azabicyclo[2.2.2]octane (120 mg, 0.449 mmol) was mixed with aqueous ammonium hydroxide (20 mL, 28%) in a sealed tube, then copper sulfate (200 mg) was added and the reaction mixture was heated at 180° C. for 14 h. The reaction mixture was allowed to cool to ambient temperature and then extracted with chloroform (4×20 mL). The combined organic extracts were dried ($K_2CO_3$), filtered and concentrated by rotary evaporation to afford a dark syrup. This crude product was subjected to column chromatography, using chloroform methanol: triethylamine (9:1:1) as eluent, to yield 2-(5-amino-3-pyridyl)-1-azabicyclo[2.2.2]octane as a light brown solid (20 mg). An impure fraction was also obtained, which afforded a brown solid (40 mg), found to be mostly the desired compound with minor impurities (total yield ~65%). A sample of the free base (20 mg, 0.098 mmol) was dissolved in ethanolic HCl (2 mL) and the mixture sonicated for 5 min. The solvent was removed by rotary evaporation to yield a viscous oil, which solidified upon standing. Recrystallization from ethanol: ether (9:1) afforded the trihydrochloride salt of the product as a brown solid (20 mg), m.p. 210° C. with decomposition.

Example 7

Sample No. 7 is 2-(5-ethoxy-3-pyridyl)-1-azabicyclo[2.2.2]octane dihydrochloride, which was prepared according to the following techniques.

2-(5-Ethoxy-3-pyridyl)-1-azabicyclo[2.2.2]octane dihydrochloride

To a stirred solution of 2-(5-amino-3-pyridyl)-1-azabicyclo[2.2.2]octane trihydrochloride (25 mg, 0.08 mmol) in dry ethanol (3 mL) was added isoamyl nitrite (0.10 mL, 0.74 mmol) and the mixture was refluxed for 2 h. When TLC analysis of the reaction mixture showed absence of starting material, the mixture was allowed to cool to ambient temperature. The solvent was removed by rotary evaporation to yield a thick brown oil, which solidified upon addition of dry diethyl ether. The product thus obtained was dissolved in chloroform and kept overnight at 4° C. to induce crystallization. The resulting solids were filtered, washed with diethyl ether and finally dried under vacuum for 24 h, to yield 2-(5-ethoxy-3-pyridyl)-1-azabicyclo[2.2.2]octane dihydrochloride (10 mg, 51%) as colorless needles.

Example 8

Sample No. 8 is 2-(5-isopropoxy-3-pyridyl)-1-azabicyclo[2.2.2]octane dihydrochloride, which was prepared according to the following techniques.

2-(5-Isopropoxy-3-pyridyl)-1-azabicyclo[2.2.2]octane dihydrochloride

To a stirred solution of 2-(5-amino-3-pyridyl)-1-azabicyclo[2.2.2]octane trihydrochloride (50 mg, 0.16 mmol) in dry isopropanol (5 mL) was added isoamyl nitrite (0.1 mL, 0.97 mmol) and the reaction mixture was refluxed for 2 h. When TLC analysis of the reaction mixture showed the absence of starting material, the mixture was allowed to warm to ambient temperature and then the solvent was removed under vacuum. A white solid was obtained upon the addition of dry diethyl ether. The solid was dissolved with heating in a minimum amount of chloroform, and the solution kept over night at 4° C. to induce crystallization. The solid thus obtained was filtered and dried under vacuum for 24 h to afford 2-(5-isopropoxy-3-pyridyl)-1-azabicyclo[2.2.2]octane dihydrochloride (28 mg, 55%) as colorless needles.

Example 9

Sample No. 9 is 2-(3-pyridyl)-1-azabicyclo[3.2.2]nonane dihydrochloride, which was prepared according to the following techniques.

4-(Bromomethyl)oxane (4-Oxanyl)methyl methanesulfonate (12.0 g, 62 mmol) was dissolved in dry acetone (50 mL) and then lithium bromide (32.2 g, 371 mmol) was added. The reaction mixture was refluxed for 6 h under a $N_2$ atmosphere. The solvent was removed by rotary evaporation. The residue obtained was mixed with water (25 mL) and extracted with dichloromethane (3×25 mL). The combined organic extracts were dried ($K_2CO_3$), filtered and concentrated by rotary evaporation. The resulting dark brown liquid was distilled (65–70° C., 5 mm) to afford 9.0 g of a colorless liquid (81% yield).

2-(-3-Pyridyl)-3-aza-4-methylpent-2-ene 2-(3-Pyridyl)-3-aza-4-methylpent-2-ene was synthesized according to the literature procedure (Kimpe, et al., *Tet. Lett.* 34(29): 4693 (1993)). To a stirring solution of 3-acetylpyridine (8.10 g, 66.9 mmol) and isopropylamine (39.5 g, 669 mmol) in dry THF (200 mL) at −10° C. under $N_2$ was added titanium tetrachloride (9.52 g, 50.2 mmol) drop-wise from a dropping funnel (Caution! The reaction is very exothermic!). The reaction mixture, now containing a dark red precipitate, was warmed to ambient temperature as it stirred overnight. Saturated aqueous $Na_2CO_3$ (200 mL) was added and the mixture was extracted with dichloromethane (3×100 mL). The combined organic extracts were dried ($Na_2SO_4$), filtered and concentrated by rotary evaporation. The residue, a dark brown viscous liquid, was distilled by short path distillation (90°–95° C., 3 mm) to afford a colorless liquid (8.13 g, 75% yield).

1-(3-Pyridyl)-3-(4-oxanyl)propan-1-one

Lithium diisopropylamide was prepared from diisopropylamine (2.82 g, 3.89 mL, 27.9 mmol) in dry THF (25 mL) and 2.5 M n-butyllithium in hexane (11.2 mL) at 0° C. under a $N_2$ atmosphere. This was added drop-wise via cannula, over a period of 15 min, to a stirring solution of 2-(3-pyridyl)-3-aza-4-methylpent-2-ene (3.48 g, 21.5 mmol) in dry THF (50 mL) at 0° C. under a $N_2$ atmosphere. The mixture was stirred an additional 30 min, then 4-(bromomethyl)oxane (3.88 g, 21.7 mmol) in dry THF (20 mL) was added drop-wise via cannula over a period of 15 min at 0° C. The reaction mixture was stirred overnight as it warmed to ambient temperature. Saturated aqueous $NH_4Cl$ solution (25 mL) was added and the mixture was stirred for another 45 min. It was then extracted with chloroform (4×40 mL). The combined organic extracts were dried ($Na_2SO_4$), filtered and concentrated by rotary evaporation. The resulting light brown viscous liquid was purified by column chromatography, using chloroform: acetone (3:2, v/v) as the eluent, to yield 4.46 g (95% yield) of a viscous tan liquid.

1-(3-Pyridyl)-3-(4-oxanyl)propan-1 one oxime

To 1-(3-pyridyl)-3-(4-oxanyl)propan-1-one (3.00 g, 13.7 mmol) was added saturated aqueous $Na_2CO_3$ (25 mL) and hydroxylamine hydrochloride (5.71 g, 82.2 mmol) in small portions. Solid $K_2CO_3$ was added to make the solution basic (pH>10). The reaction mixture was stirred overnight at ambient temperature and extracted with chloroform (4×40 mL). The combined organic extracts were dried ($Na_2SO_4$), filtered and concentrated by rotary evaporation. The resulting colorless viscous liquid (3.00 g, 93.8%) solidified upon standing at ambient temperature.

1-(3-Pyridyl)-3-(4-oxanyl)propylamine

Acetic acid (16 mL) was added to a suspension of 1-(3-pyridyl)-3-(4-oxanyl)propan-1-one oxime (1.60 g, 6.83 mmol) in 95% ethanol (40 mL) over a period of 15 min. Zinc dust (12 g, 180 mmol) was added and the reaction mixture was stirred at ambient temperature for 4 h. The reaction mixture was filtered through a Celite plug, which was then washed with ethanol (50 mL). The combined filtrates were concentrated by rotary evaporation. The solid residue was made basic by addition of 50% aqueous NaOH (with ice bath cooling), saturated with solid NaCl and extracted with chloroform (5×30 mL). The combined organic extracts were dried ($Na_2SO_4$), filtered and concentrated by rotary evaporation to give pure product as a colorless viscous liquid (1.40 g, 82% yield).

2-(3-Pyridyl)-1-azabicyclo[3.2.2]nonane dihydrochloride

A solution of 1-(3-pyridyl)-3-(4-oxanyl)propylamine (1.00 g, 4.54 mmol) in 48% aqueous HBr (15 mL) was saturated with HBr gas. The mixture was heated in a pressure tube at 100°–120° C. for 12 h. The tube was cooled in ice water and the contents transferred to a 250 mL round bottom flask. Removal of the volatiles by rotary evaporation afforded a light yellow solid. Absolute ethanol (200 mL) and solid $K_2CO_3$ (10 g) were added and the mixture was heated at reflux for 8 h. The mixture was filtered through a Celite plug, which was then washed with ethanol (25 mL). The combined filtrates were concentrated by rotary evaporation; the solid obtained was suspended in saturated aqueous NaCl (10 mL) and extracted with chloroform (4×30 mL). The combined organic extracts were dried ($K_2CO_3$), filtered and concentrated by rotary evaporation to give a dark brown oil. Short path distillation (120°–122° C., 2 mm) provided 0.750 g of the desired free base as a colorless oil (81.7% yield).

A portion (0.500 g, 2.48 mmol) of the free base was dissolved in 2 mL of concentrated HCl and sonicated for 2 min. The excess aqueous HCl was removed by repeated azeotropic rotary evaporation using portions of ethanol. The resulting solid was recrystallized from isopropanol and ether to give colorless needles (0.560 g, 82.3% yield).

Example 10

Sample No. 10 is (R)-2-(3-pyridyl)-1-azabicyclo[3.2.2]nonane hydrochloride, which was prepared according to the following techniques.

Ethyl 2-(4-oxanylidene)acetate

To a suspension of sodium hydride (80% in oil, 4.24 g, 141 mmol) in dry benzene (50 mL) was added drop-wise over 30 min a solution of triethylphosphonoacetate (31.7 g, 141 mmol) in benzene (25 mL). After stirring for 30 min, oxan-4-one (tetrahydropyran-4-one) (14.0 g, 140 mmol) in benzene (50 mL) was added drop-wise over a 45 min period, allowing the reaction temperature to rise to 40° C. Then the mixture was stirred at 60° C. for 1 h. A further equivalent of sodium hydride (4.24 g, 141 mmol) was added in 3 portions at 15 min intervals. After a further 15 min, the reaction mixture was cooled to room temperature and quenched with water (50 mL). The layers were separated and the aqueous layer extracted with ethyl acetate (2×50 mL). The combined organic extracts were dried ($Na_2SO_4$), filtered and concentrated by rotary evaporation to give the desired ester as a light brown oil (22.0 g, 92%).

Ethyl 2-(4-oxanyl)acetate

To a solution of ethyl 2-(4-oxanylidene)acetate (22.0 g, 139 mmol) in ethanol (50 mL) was added 10% Pd/C (2.2 g) and the mixture subjected to hydrogenation overnight on a Parr apparatus (50 psi). The catalyst was removed by filtration through Celite, which was washed with ethanol (25 mL). Removal of solvent from the combined filtrates by rotary evaporation gave the desired product as a colorless oil (22.0 g, 98.5%).

2-(4-Oxanyl)ethanol

To a stirring suspension of lithium aluminum hydride (5.10 g, 138 mmol) in THF (200 mL) at 0° C. was added drop-wise a solution of ethyl 2-(4-oxanyl)acetate (22.0 g, 138 mmol) in THF (50 mL). The reaction mixture was then heated at reflux overnight. After cooling the mixture in an ice bath, ether (300 mL) was added, followed by drop-wise addition of 5N NaOH, until the formation of heavy white precipitate is complete. The suspension was filtered and the filtrate dried ($K_2CO_3$), filtered and concentrated by rotary evaporation to give a colorless liquid (17.7 g, 100%).

2-(4-Oxanyl)ethyl methanesulfonate

To a stirring solution of 2-(4-oxanyl)ethanol (9.63 g, 74.0 mmol) in dry dichloromethane (350 mL) was added distilled triethylamine (20.62 mL, 96.2 mmol) at 0° C., followed by drop-wise addition of methanesulfonyl chloride (7.44 mL, 96.2 mmol) over 15 min. The reaction was stirred for 16 h under $N_2$ and slowly allowed to come to ambient temperature. The reaction was washed with saturated $NaHCO_3$ (100 mL) and the aqueous phase was extracted with dichloromethane (1×50 mL). The combined organic extracts were dried ($K_2CO_3$), filtered and concentrated by rotary evaporation to yield 11.9 g of a colorless oil (77.0% yield).

4-(2-Bromoethyl)oxane

To a stirring solution of 2-(4-oxanyl)ethyl methanesulfonate (11.9 g, 56.9 mmol) in dry acetone (300 mL) was added lithium bromide (29.7 g, 56.9 mmol). The reaction was refluxed under an $N_2$ atmosphere for 5 h. The acetone was removed by rotary evaporation, water (150 mL) was added and the mixture was extracted with dichloromethane (2×100 mL). The combined extracts were dried ($K_2CO_3$), filtered and concentrated by rotary evaporation to yield a light brown oil. The crude compound was then distilled (65° C., 0.2 mm) to yield 8.06 g of a colorless oil (73.3% yield).

2,6,6-Trimethyl-3-(3-pyridylmethylimino)bicyclo[3.1.1]heptan-2-ol

To a stirring solution of (−)-2-hydroxy-3-pinanone (10.00 g, 59.4 mmol) in benzene (500 mL) was added 3-pyridylmethylamine (6.66 mL, 65.4 mmol) in one portion. Boron trifluoride diethyletherate (0.7 mL, 5.9 mmol) was added in one portion and the reaction was refluxed under $N_2$ for 5 h, then stirred at room temperature for an additional 16 h. The benzene was removed by rotary evaporation and the resulting residue was stirred in saturated $NaHCO_3$ solution (100 mL) for 1 h. This was then extracted with chloroform (3×100 mL), and the combined extracts dried ($Na_2SO_4$), filtered and concentrated by rotary evaporation. The resulting dark brown oil was purified by column chromatography, using a chloroform:methanol gradient (5:1 to 1:1, v/v) as eluent. The light yellow oil was crystallized by dissolving in hot ethyl acetate (50 mL) and placed in a freezer at −4° C. for 16 h. After warming to room temperature, the crystals were filtered, washed with ice-cold ethyl acetate, and dried on a hi-vacuum pump to yield off-white crystals (8.04 g, 52.4% yield).

2,6,6-Trimethyl-3-(1-(3-pyridyl)-3-(4-oxanyl)propylimino)bicyclo[3.1.1]heptan-2-ol Lithium diisopropylamide (LDA) was prepared by adding 2.5 M n-butyllithium (6.23 mL, 15.6 mmol) to a solution of diisopropylamine (2.19 mL, 15.6 mmol) in dry THF (20 mL) at 0° C. The solution was allowed to come to ambient temperature and stir for 30 min. The LDA was added drop-wise via cannula to a stirring solution of 2,6,6-trimethyl-3-(3-pyridylmethylimino)-bicyclo[3.1.1]heptan-2-ol (2.00 g, 7.8 mmol) in dry THF (80 mL) at −78° C. This solution was stirred for 1 h at −78° C., at which point a solution of 4-(2-bromoethyl)oxane (2.69 g, 14.0 mmol) in THF (50 mL) was added drop-wise. The solution was allowed to slowly come to ambient temperature and stir for 16 h. Saturated aqueous NH$_4$Cl solution (100 mL) was added and the mixture stirred for 30 min. The layers were separated and the aqueous layer was extracted with chloroform (2×50 mL). The combined organic extracts were dried (K$_2$CO$_3$), filtered and concentrated by rotary evaporation. The resulting material was purified by column chromatography, using chloroform:acetone (3:1, v/v) as eluent, to yield 1.85 g of a yellow oil (64.5% yield).

(R)-1-(3-Pyridyl)-3-(4-oxanyl)-propylamine

To a solution of 2,6,6-trimethyl-3-(1-(3-pyridyl)-3-(4-oxanyl)propylimino]bicyclo[3.1.1]heptan-2-ol (1.85 g, 5.0 mmol) in ethanol (20 mL) was added hydroxylamine hydrochloride (2.00 g, 28.8 mmol) and K$_2$CO$_3$ (3.98 g, 28.8 mmol) and the mixture was heated to reflux for 16 h. The reaction was then cooled to room temperature, filtered through Celite, washed with ethanol, concentrated by rotary evaporation and purified by column chromatography, using a gradient of chloroform:methanol:ammonium hydroxide (90:9:1 to 80:19:1) eluent, to yield 0.88 g of a light yellow oil (80% yield).

(R)-2-(3-Pyridyl)-1-azabicyclo[3.2.2]nonane dihydrochloride

A solution of (R)-1-(3-pyridyl)-3-(4-oxanyl)propylamine (0.88 g, 4.0 mmol) in 48% aqueous HBr (20 mL) was saturated with HBr gas. The mixture was heated in a pressure tube at 120° C. for 12 h. The tube was cooled in ice water and the contents transferred to a round bottom flask. Removal of the volatiles by rotary evaporation afforded a light brown solid. Absolute ethanol (250 mL) and solid K$_2$CO$_3$ (20 g) were added and the mixture was heated at reflux for 16 h. The mixture was cooled and filtered through a Celite pad, which was then washed with ethanol (25 mL). The combined filtrates were concentrated by rotary evaporation and the solid obtained was suspended in saturated aqueous NaCl (20 mL) and extracted with chloroform (5×20 mL). The combined organic extracts were dried (Na$_2$SO$_4$), filtered and concentrated by rotary evaporation to give a dark brown oil. The oil was purified by column chromatography, using chloroform:methanol:ammonium hydroxide (90:9:1, v/v) as eluent, then distilled on a Kugelrohr apparatus to provide 528 mg of the desired free base as a light yellow oil (65.3% yield).

The free base was dissolved in a solution of ethanol (5 mL) and concentrated HCl (2 mL). The excess aqueous HCl was removed by repeated azeotropic rotary evaporation using portions of ethanol. The resulting solid was recrystallized from ethanol and ether to give 227 mg (40.6% yield) of (R)-2-pyridin-3-yl-1-azabicyclo[3.2.2]nonane dihydrochloride as an off-white solid, m.p. 258–260° C.

Example 11

Sample No. 11 is (S)-2-(3-pyridyl)-1-azabicyclo[3.2.2]nonane hydrochloride, which was prepared according to the following procedures.

2,6,6-Trimethyl-3-(3-pyridylmethylimino)bicyclo[3.1.1]heptan-2-ol

To a stirring solution of (+)-2-hydroxy-3-pinanone (10.00 g, 59.4 mmol) in benzene (500 mL) was added 3-pyridylmethylamine (6.66 mL, 65.4 mmol) in one portion. Boron trifluoride diethyletherate (0.7 mL, 5.9 mmol) was added in one portion and the reaction was refluxed under N$_2$ for 5 h and then stirred at room temperature for an additional 16 h. The benzene was removed by rotary evaporation and the resulting residue was stirred in saturated NaHCO$_3$ solution (100 mL) for 1 h. This was then extracted with chloroform (3×100 mL) and the combined extracts were dried (Na$_2$SO$_4$), filtered and concentrated by rotary evaporation. The resulting dark brown oil was purified by column chromatography, using a chloroform:methanol gradient (9:1 to 1:1, v/v) as eluent. The light yellow oil was then dissolved in hot ethyl acetate (50 mL) and placed in a −4° C. freezer for 16 h. After warming to room temperature, the resulting crystals were filtered, washed with cold ethyl acetate, and dried using a hi-vacuum pump to yield 8.59 g of white powder (52.4% yield).

2,6,6-Trimethyl-3-(1-(3-pyridyl)-3-(4-oxanyl)propylimino)-bicyclo[3.1.1]heptan-2-ol Lithium diisopropylamide solution was prepared from 2.5 M n-butyllithium (6.23 mL, 15.6 mmol) and a solution of diisopropylamine (2.19 mL, 15.6 mmol) in dry THF (20 mL) at 0° C. It was allowed to come to ambient temperature and stir for 30 min. Then the LDA was added drop-wise via cannula to a solution of 2,6,6-trimethyl-3-(pyridin-3-ylmethylimino)-bicyclo[3.1.1]heptan-2-ol (2.00 g, 7.8 mmol) in dry THF (80 mL) at −78° C. This solution was stirred for 1 h at −78° C. and then a solution of 4-(2-bromo-ethyl)oxane (2.69 g, 14.0 mmol) in THF (50 mL) was added drop-wise. The solution was allowed to slowly come to ambient temperature and stir for 16 h. Then saturated aqueous NH$_4$Cl solution (100 mL) was added and the mixture stirred for 30 min. The layers were separated and the aqueous layer was extracted with chloroform (2×50 mL). The combined organic extracts were dried (K$_2$CO$_3$), filtered and concentrated by rotary evaporation. The resulting material was purified by column chromatography, using chloroform:acetone (3:1) as eluent, to yield 1.50 g as a yellow oil (52.3% yield).

(S)-1-(3-Pyridyl)-3-(4-oxanyl)propylamine

To a solution of 2,6,6-trimethyl-3-(1-(3-pyridyl)-3-(4-oxanyl)propylimino)bicyclo[3.1.1]heptan-2-ol (1.50 g, 4.0 mmol) in ethanol (20 mL) was added hydroxylamine hydrochloride (2.00 g, 28.8 mmol) and K$_2$CO$_3$ (3.98 g, 28.8 mmol) and the mixture was refluxed for 16 h. The reaction was then cooled to room temperature, filtered through Celite, washed with ethanol, and concentrated by rotary evaporation. It was purified by column chromatography, using a chloroform:methanol:ammonium hydroxide gradient (90:9:1 to 80:19:1, v/v) as eluent, to yield 0.65 g as a light yellow oil (73% yield).

(S)-2-(3-Pyridyl)-1-azabicyclo[3.2.2]nonane dihydrochloride

A solution of (S)-1-(3-pyridyl)-3-(4-oxanyl)propylamine (0.65 g, 4.0 mmol) in 48% aqueous HBr (20 mL) was saturated with HBr gas. The mixture was heated in a pressure tube at 120° C. for 12 h. The tube was cooled in ice water and the contents transferred to a round bottom flask.

Removal of the volatiles by rotary evaporation afforded a light brown solid. Absolute ethanol (250 mL) and solid $K_2CO_3$ (20 g) were added and the mixture was heated at reflux for 16 h. The mixture was cooled to room temperature and filtered through a Celite pad, which was then washed with ethanol (25 mL). The combined filtrates were concentrated by rotary evaporation and then the solid obtained was suspended in saturated aqueous NaCl (20 mL) and extracted with chloroform (5×20 mL). The combined chloroform extracts were dried ($Na_2SO_4$), filtered and concentrated by rotary evaporation to give a dark brown oil. This was purified by column chromatography, using chloroform:methanol:ammonium hydroxide (90:9:1, v/v) as eluent, and then distilled on a Kugelrohr apparatus to provide 386.4 mg of the desired free base as a colorless oil (64.72% yield).

The free base was dissolved in ethanol (5 mL) and then concentrated HCl (2 mL) was added. The excess aqueous HCl was removed by repeated azeotropic rotary evaporation using portions of ethanol. The remaining solid was recrystallized from ethanol and ether to give 123.0 mg (45.61% yield) of (S)-2-(3-pyridyl)-1-azabicyclo[3.2.2]nonane dihydrochloride as a white solid, m.p. 258–260° C.

V. Biological Assays

Example 12

Radioligand Binding at CNS nAChRs

α4β2 nAChR Subtype

Rats (female, Sprague-Dawley), weighing 150–250 g, were maintained on a 12 h light/dark cycle and were allowed free access to water and food supplied by PMI Nutrition International, Inc. Animals were anesthetized with 70% $CO_2$, then decapitated. Brains were removed and placed on an ice-cold platform. The cerebral cortex was removed and placed in 20 volumes (weight:volume) of ice-old preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 μM, was added and the suspension was homogenized by Polytron. The homogenate was centrifuged at 18,000×g for 20 min at 4° C. and the resulting pellet was re-suspended in 20 volumes of ice-cold water. After 60 min incubation on ice, a new pellet was collected by centrifugation at 18,000×g for 20 min at 4° C. The final pellet was re-suspended in 10 volumes of buffer and stored at −20° C. On the day of the assay, tissue was thawed, centrifuged at 18,000×g for 20 min, and then re-suspended in ice-cold PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4) to a final concentration of approximately 4 mg protein/mL. Protein was determined by the method of Lowry et al., *J. Biol. Chem.* 193: 265 (1951), using bovine serum albumin as the standard.

The binding of [$^3$H]nicotine was measured using a modification of the methods of Romano et al., *Science* 210: 647 (1980) and Marks et al., *Mol. Pharmacol.* 30: 427 (1986). The [$^3$H]nicotine (Specific Activity=81.5 Ci/mmol) was obtained from NEN Research Products. The binding of [$^3$H]nicotine was measured using a 3 h incubation at 4° C. Incubations were conducted in 48-well micro-titre plates and contained about 400 μg of protein per well in a final incubation volume of 300 μL. The incubation buffer was PBS and the final concentration of [$^3$H]nicotine was 5 nM. The binding reaction was terminated by filtration of the protein containing bound ligand onto glass fiber filters (GF/B, Brandel) using a Brandel Tissue Harvester at 4° C. Filters were soaked in de-ionized water containing 0.33% polyethyleneimine to reduce non-specific binding. Each filter was washed with ice-cold buffer (3×1 mL). Non-specific binding was determined by inclusion of 10 μM non-radioactive L-nicotine (Acros Organics) in selected wells.

The inhibition of [$^3$H]nicotine binding by test compounds was determined by including seven different concentrations of the test compound in selected wells. Each concentration was replicated in triplicate. $IC_{50}$ values were estimated as the concentration of compound that inhibited 50 percent of specific [$^3$H]nicotine binding. Inhibition constants (Ki values), reported in nM, were calculated from the $IC_{50}$ values using the method of Cheng et al., *Biochem. Pharmacol.* 22: 3099 (1973).

For initial screening, a single concentration of test compounds was tested in the above assay format with the following modifications. The binding of [$^3$H]epibatidine was measured. The [$^3$H]epibatidine (Specific Activity=48 Ci/mmol) was obtained from NEN Research Products. The binding of [$^3$H]epibatidine was measured using a 2 h incubation at 21° C. (room temperature). Incubations were conducted in 96-well Millipore Multiscreen (MAFB) plates containing about 200 μg of protein per well in a final incubation volume of 150 μL. The incubation buffer was PBS and the final concentration of [$^3$H]epibatidine was 0.3 nM. The binding reaction was terminated by filtration of the protein containing bound ligand onto the glass fiber filter base of the Multiscreen plates. Filters were soaked in de-ionized water containing 0.33% polyethyleneimine to reduce non-specific binding. Each filter was washed with ice-cold buffer (3×0.25 mL). Non-specific binding was determined by inclusion of 10 μM non-radioactive L-nicotine (Acros Organics) in selected wells. The single concentration of test compound was 5 μM and testing was performed in triplicate. 'Active' compounds were defined as compounds that inhibited the binding of [$^3$H]epibatidine to the receptor by at least 50% compared with the binding of [$^3$H]epibatidine in the absence of competitor. For those compounds found to be active in the single point screen, the inhibition constants (Ki values) were determined as described in the previous paragraphs of this section.

α7 nAChR Subtype

Rats (female, Sprague-Dawley), weighing 150–250 g, were maintained on a 12 h light/dark cycle and were allowed free access to water and food supplied by PMI Nutrition International, Inc. Animals were anesthetized with 70% $CO_2$, then decapitated. Brains were removed and placed on an ice-cold platform. The hippocampus was removed and placed in 10 volumes (weight:volume) of ice-cold preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 μM, was added and the tissue suspension was homogenized by Polytron. The homogenate was centrifuged at 18,000×g for 20 min at 4° C. and the resulting pellet was re-suspended in 10 volumes of ice-cold water. After 60 min incubation on ice, a new pellet was collected by centrifugation at 18,000× g for 20 min at 4° C. The final pellet was re-suspended in 10 volumes of buffer and stored at −20° C. On the day of the assay, tissue was thawed, centrifuged at 18,000×g for 20 min, and then resuspended in ice-cold PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM MgCl$_2$, Invitrogen/Gibco, pH 7.4) to a final concentration of approximately 2 mg protein/mL. Protein was determined by the method of Lowry et al., *J. Biol. Chem.* 193: 265 (1951), using bovine serum albumin as the standard.

The binding of [$^3$H]MLA was measured using a modification of the methods of Davies et al., *Neuropharmacol.* 38: 679 (1999). [$^3$H]MLA (Specific Activity=25–35 Ci/mmol) was obtained from Tocris. The binding of [$^3$H]MLA was determined using a 2 h incubation at 21° C. Incubations were conducted in 48-well micro-titre plates and contained about 200 μg of protein per well in a final incubation volume of 300 μL. The incubation buffer was PBS and the final concentration of [$^3$H]MLA was 5 nM. The binding reaction was terminated by filtration of the protein containing bound ligand onto glass fiber filters (GF/B, Brandel) using a Brandel Tissue Harvester at room temperature. Filters were soaked in de-ionized water containing 0.33% polyethyleneimine to reduce non-specific binding. Each filter was washed with PBS (3×1 mL) at room temperature. Non-specific binding was determined by inclusion of 50 μM non-radioactive MLA in selected wells.

The inhibition of [$^3$H]MLA binding by test compounds was determined by including seven different concentrations of the test compound in selected wells. Each concentration was replicated in triplicate. IC$_{50}$ values were estimated as the concentration of compound that inhibited 50 percent of specific [$^3$H]MLA binding. Inhibition constants (Ki values), reported in nM, were calculated from the IC$_{50}$ values using the method of Cheng et al., *Biochem. Pharmacol.* 22: 3099–3108 (1973).

For initial screening, a single concentration of test compounds was tested in the above assay format with the following modifications. Incubations were conducted in 96-well plates in a final incubation volume of 150 μL. Once the binding reaction was terminated by filtration onto glass fiber filters, the fillers were washed four times with approximately 250 μL of PBS at room temperature. Non-specific binding was determined by inclusion of 10 μM non-radioactive MLA in selected wells. The single concentration of test compound was 5 μM and testing was performed in triplicate. 'Active' compounds were defined as compounds that inhibited the binding of [$^3$H]MLA to the receptor by at least 50% compared with the binding of [$^3$H]MLA in the absence of competitor. For those compounds found to be active in the single point screen, the inhibition constants (Ki values) were determined as described in the previous paragraphs of this section.

Determination of Dopamine Release

Dopamine release was measured using striatal synaptosomes obtained from rat brain, according to the procedures set forth by Rapier et al., *J. Neurochem.* 54: 937 (1990). Rats (female, Sprague-Dawley), weighing 150–250 g, were maintained on a 12 h light/dark cycle and were allowed free access to water and food supplied by PMI Nutrition International, Inc. Animals were anesthetized with 70% CO$_2$, then decapitated. The brains were quickly removed and the striata dissected. Striatal tissue from each of 2 rats was pooled and homogenized in ice-cold 0.32 M sucrose (5 mL) containing 5 mM HEPES, pH 7.4, using a glass/glass homogenizer. The tissue was then centrifuged at 1,000×g for 10 min. The pellet was discarded and the supernatant was centrifuged at 12,000×g for 20 min. The resulting pellet was re-suspended in perfusion buffer containing monoamine oxidase inhibitors (128 mM NaCl, 1.2 mM KH$_2$PO$_4$, 2.4 mM KCl, 3.2 mM CaCl$_2$, 1.2 mM MgSO$_4$, 25 mM HEPES, 1 mM ascorbic acid, 0.02 mM pargyline HCl and 10 mM glucose, pH 7.4) and centrifuged for 15 min at 25,000×g. The final pellet was resuspended in perfusion buffer (1.4 mL) for immediate use.

The synaptosomal suspension was incubated for 10 min at 37° C. to restore metabolic activity. [$^3$H]Dopamine ([$^3$H] DA, specific activity=28.0 Ci/mmol, NEN Research Products) was added at a final concentration of 0.1 μM and the suspension was incubated at 37° C. for another 10 min. Aliquots of tissue (50 μL) and perfusion buffer (100 μL) were loaded into the suprafusion chambers of a Brandel Suprafusion System (series 2500, Gaithersburg, Md.). Perfusion buffer (room temperature) was pumped into the chambers at a rate of 3 mL/min for a wash period of 8 min. Test compound (10 μM) or nicotine (10 μM) was then applied in the perfusion stream for 40 sec. Fractions (12 sec each) were continuously collected from each chamber throughout the experiment to capture basal release and agonist-induced peak release and to re-establish the baseline after the agonist application. The perfusate was collected directly into scintillation vials, to which scintillation fluid was added. [$^3$H]DA released was quantified by scintillation counting. For each chamber, the integrated area of the peak was normalized to its baseline.

Release was expressed as a percentage of release obtained with an equal concentration of L-nicotine. Within each assay, each test compound was replicated using 2–3 chambers; replicates were averaged. When appropriate, dose-response curves of test compound were determined. The maximal activation for individual compounds (Emax) was determined as a percentage of the maximal activation induced by L-nicotine. The compound concentration resulting in half maximal activation (EC$_{50}$) of specific ion flux was also defined.

Example 13

Selectivity vs. Peripheral nAChRs

Interaction at the Human Muscle nAChR Subtype

Activation of muscle-type nAChRs was established on the human clonal line TE671/RD, which is derived from an embryonal rhabdomyosarcoma (Stratton et al., *Carcinogen* 10: 899 (1989)). These cells express receptors that have pharmacological (Lukas, *J. Pharmacol. Exp. Ther.* 251: 175 (1989)), electrophysiological (Oswald et al., *Neurosci. Lett.* 96: 207 (1989)), and molecular biological profiles (Luther et al., *J. Neurosci.* 9: 1082 (1989)) similar to the muscle-type nAChR.

TE671/RD cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells were cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells were 80% confluent, they were plated to 6 well polystyrene plates (Costar). Experiments were conducted when the cells reached 100% confluency.

Nicotinic acetylcholine receptor (nAChR) function was assayed using $^{86}$Rb$^+$ efflux according to the method described by Lukas et al., *Anal. Biochem.* 175: 212 (1988). On the day of the experiment, growth media was gently removed from the well and growth media containing $^{86}$Rubidium chloride (10$^6$ μCi/mL) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH. 7.4), taking care not to disturb the cells. Next, cells were exposed to either 100 μM of test compound, 100 μM of L-nicotine (Acros Organics) or buffer alone for 4 min. Following the exposure period, the supernatant containing the released $^{86}Rb^+$ was removed and transferred to scintillation vials. Scintillation fluid was added and released radioactivity was measured by liquid scintillation counting.

Within each assay, each point had 2 replicates, which were averaged. The amount of $^{86}Rb^+$ release was compared to both a positive control (100 μM L-nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also determined.

Interaction at the Rat Ganglionic nAChR Subtype

Activation of rat ganglion nAChRs was established on the pheochromocytoma clonal line PC12, which is a continuous clonal cell line of neural crest origin, derived from a tumor of the rat adrenal medulla. These cells express ganglion-like nAChRs (see Whiting et al., *Nature* 327: 515 (1987); Lukas, *J. Pharmacol. Exp. Ther.* 251: 175 (1989); Whiting et al., *Mol. Brain Res.* 10: 61 (1990)).

Rat PC12 cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells were cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells were 80% confluent, they were plated to 6 well Nunc plates (Nunclon) and coated with 0.03% poly-L-lysine (Sigma, dissolved in 100 mM boric acid). Experiments were conducted when the cells reached 80% confluency.

Nicotinic acetylcholine receptor (nAChR) function was assayed using $^{86}Rb^+$ efflux according to a method described by Lukas et al., *Anal. Biochem.* 175: 212 (1988). On the day of the experiment, growth media was gently removed from the well and growth media containing $^{86}$Rubidium chloride ($10^6$ μCi/mL) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/ Gibco, pH 7.4), taking care not to disturb the cells. Next, cells were exposed to either 100 μM of test compound, 100 μM of nicotine or buffer alone for 4 min. Following the exposure period, the supernatant containing the released $^{86}Rb^+$ was removed and transferred to scintillation vials. Scintillation fluid was added and released radioactivity was measured by liquid scintillation counting.

Within each assay, each point had 2 replicates, which were averaged. The amount of $^{86}Rb^+$ release was compared to both a positive control (100 μM nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also determined.

Interaction at the Human Ganglionic nAChR Subtype

The cell line SH-SY5Y is a continuous line derived by sequential subcloning of the parental cell line, SK-N-SH, which was originally obtained from a human peripheral neuroblastoma. SH-SY5Y cells express a ganglion-like nAChR (Lukas et al., *Mol. Cell. Neurosci.* 4: 1 (1993)).

Human SHI-SY5Y cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells were cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells were 80% confluent, they were plated to 6 well polystyrene plates (Costar). Experiments were conducted when the cells reached 100% confluency.

Nicotinic acetylcholine receptor (nAChR) function was assayed using $^{86}Rb'$ efflux according to a method described by Lukas et al., *Anal. Biochem.* 175: 212 (1988). On the day of the experiment, growth media was gently removed from the well and growth media containing $^{86}$Rubidium chloride ($10^6$ μCi/mL) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/ Gibco, pH 7.4), taking care not to disturb the cells. Next, cells were exposed to either 100 μM of test compound, 100 μM of nicotine, or buffer alone for 4 min. Following the exposure period, the supernatant containing the released $^{86}Rb^+$ was removed and transferred to scintillation vials. Scintillation fluid was added and released radioactivity was measured by liquid scintillation counting.

Within each assay, each point had 2 replicates, which were averaged. The amount of $^{86}Rb^+$ release was compared to both a positive control (100 μM nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also defined.

Example 14

Determination of Binding at Non-nicotinic Receptors Muscarinic M3 Subtype

The human clonal line TE671/RD, derived from an embryonal rhabdomyosarcoma (Stratton et al., *Carcinogen* 10: 899 (1989)), was used to define binding to the muscarinic M3 receptor subtype. As evidenced through pharmacological (Bencherif et al., *J. Pharmacol. Exp. Ther.* 257: 946 (1991) and Lukas, *J. Pharmacol. Exp. Ther.* 251: 175 (1989)), electrophysiological (Oswald et al., *Neurosci. Lett.*

96: 207 (1989)), and molecular biological studies (Luther et al., *J. Neurosci.* 9: 1082 (1989)) these cells express muscle-like nicotinic receptors.

TE671/RD cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). They were grown to confluency on 20–150 mm tissue culture treated plates. The media was then removed and cells scraped using 80 mL of PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4) and then centrifuged at 1000 rpm for 10 min. The supernatant was then suctioned off and the pellet(s) stored at −20° C. until use.

On the day of the assay, the pellets were thawed, re-suspended with PBS and centrifuged at 18,000×g for 20 min, then re-suspended in PBS to a final concentration of approximately 4 mg protein/mL and homogenized by Polytron. Protein was determined by the method of Lowry et al., *J. Biol. Chem.* 193: 265 (1951), using bovine serum albumin as the standard.

The binding of [$^3$H]QNB was measured using a modification of the methods of Bencherif et al., *J. Pharmacol. Exp. Ther.* 257: 946 (1991). [$^3$H]QNB (Specific Activity=30–60 Ci/mmol) was obtained from NEN Research Products. The binding of [$^3$H]QNB was measured using a 3 h incubation at 4° C. Incubations were conducted in 48-well micro-titre plates and contained about 400 µg of protein per well in a final incubation volume of 300 µL. The incubation buffer was PBS and the final concentration of [$^3$H]QNB was 1 nM. The binding reaction was terminated by filtration of the protein containing bound ligand onto glass fiber filters (GF/B, Brandel) using a Brandel Tissue Harvester at 4° C. Filters were pre-soaked in de-ionized water containing 0.33% polyethyleneimine to reduce non-specific binding. Each filter was washed with ice-cold buffer (3×1 mL). Non-specific binding was determined by inclusion of 10 µM non-radioactive atropine in selected wells. The inhibition of [$^3$H]QNB binding by test compounds was determined by including seven different concentrations of the test compound in selected wells. Each concentration was replicated in triplicate. $IC_{50}$ values were estimated as the concentration of compound that inhibited 50 percent of specific [$^3$H]QNB binding. Inhibition constants (Ki values), reported in nM, were calculated from the $IC_{50}$ values using the method of Cheng et al., *Biochem. Pharmacol.* 22: 3099 (1973).

Example 15

Determination of Activity at the α7 nAChR Subtype

Selective α7 agonists can be found using a functional assay on FLIPR (see, for example, PCT WO 00/73431 A2, the contents of which are hereby incorporated by reference), which is a commercially available high throughput assay (Molecular Devices Corporation, Sunnyvale, Calif.). FLIPR is designed to read the fluorescent signal from each well of a 96 or 384 well plate as fast as twice a second for up to 30 minutes. This assay can be used to accurately measure the functional pharmacology of α7 nAChR and $5HT_3R$ subtypes. Cell lines that express functional forms of the α7 nAChR subtype using the α7/5-$HT_3$ channel as the drug target and/or cell lines that express functional 5-$HT_3$ are used to conduct the assay. In both cases, the ligand-gated ion channels are expressed in SH-EP1 cells. Both ion channels can produce a robust signal in the FLIPR assay. Using the FLIPR assay, the compounds described herein can be evaluated for their ability to function as agonists, partial agonists or antagonists at the α7 nAChR subtype.

Example 16

Summary of Biological Activity

The compounds in Examples 1–8 were evaluated using the techniques described above. For comparison purposes, sample No. C-1 is (S)-(–)-nicotine, which has been reported to have demonstrated a positive effect toward the treatment of various CNS disorders. The data is summarized below in Table 1.

TABLE 1

| Sample No. | Log P | Ki (nM) | Dopamine Release | | Muscle Effect | | Ganglion Effect | |
|---|---|---|---|---|---|---|---|---|
| | | | $EC_{50}$ | $Ec_{max}$ | $EC_{50}$ | $Ec_{max}$ | $EC_{50}$ | $Ec_{max}$ |
| 1 | 1.26 | 2 | 2 | 40 | 59 | 110 | 1,100 | 85 |
| 2 | 2.05 | 1 | 2 | 43 | 3,000 | 133 | 3,000 | 106 |
| 3 | 0.94 | 0.5 | 6 | 130 | 100 | 130 | 150 | 100 |
| 4 | 0.94 | 2.5 | 33 | 114 | 100 | 130 | 150 | 100 |
| 5 | 0.93 | 7 | 4 | 93 | 300 | 130 | N/A | 120 |
| 6 | 0.48 | 2.6 | 7 | 43 | 3,000 | 100 | 10,000 | 75 |
| 7 | 1.82 | 1 | 5 | 40 | 700 | 137 | 10,000 | 86 |
| 8 | 1.76 | 0.4 | 31 | 31 | 3,000 | 115 | 10,000 | 94 |
| C-1* | 0.71 | 2 | 115 | 100 | 60,000 | 100 | 20,000 | 100 |

*Not an example of the invention.
N/A-Not available.

The data in Table 1 indicate that the compounds of the present invention have the capability to selectively bind with high affinity to certain CNS nicotinic receptors as indicated by their low binding constants, and the capability to selectively activate certain CNS receptors and cause neurotransmitter release, as evidenced by dopamine release, thereby demonstrating known nicotinic pharmacology. The data further indicate that certain compounds activate dopamine release at concentrations well below those concentrations required for activation of muscle or ganglionic receptors. Thus, the data indicate that the compounds of the present invention have the capability of being useful in treating CNS disorders involving nicotinic cholinergic systems. Furthermore, the data indicate that certain compounds of the present invention do not cause any appreciable side effects at muscle sites or ganglionic sites at concentrations effective for producing CNS effects or neurotransmitter release, thus indicating a lack of undesirable side effects in subjects receiving administration of those compounds at dose ranges at which CNS effects and neurotransmitter release are elicited.

The data indicate that the compounds of the present invention have the capability to activate human CNS receptors without activating muscle-type or ganglionic-type nicotinic acetylcholine receptors. The data show that the compounds of the present invention provide a therapeutic window for utilization in the treatment of CNS disorders. That is, at the levels that the compounds of the present invention are employed, those compounds show CNS effects and/or neurotransmitter release effects to a significant degree but do not show undesirable muscle or ganglionic effects to any significant degree. The data show that certain compounds of the present invention, particularly Sample Nos. 2, 6 and 8, begin to cause muscle effects and effects upon ganglia only when employed in amounts of many times those required to cause dopamine release.

The foregoing is illustrative of the present invention and is not to be construed as limiting thereof. The invention is defined by the following claims, with equivalents of the claims to be included therein.

That which is claimed is:

1. A compound selected from the group consisting of (R)-2-(3-pyridyl)-1-azabicyclo[3.2.2]nonane, (S)-2-(3-pyridyl)-1-azabicyclo[3.2.2]nonane, and mixtures thereof.

2. A pharmaceutical composition comprising a compound of claim 1 and a pharmaceutically acceptable carrier.

* * * * *